(12) United States Patent
Srivastava et al.

(10) Patent No.: US 7,932,287 B2
(45) Date of Patent: Apr. 26, 2011

(54) THERAPEUTIC COMPOSITIONS AND USES

(75) Inventors: Suresh C. Srivastava, Burlington, MA (US); Sant K. Srivastav, Burlington, MA (US); Stanley J. Szymanski, Jr., Sewickley, PA (US)

(73) Assignees: ChemGenes Corporation, Wilmington, MA (US); Stanley J. Szymanski, Jr., Sewickley, PA (US)

( * ) Notice: Subject to any disclaimer, the term of this patent is extended or adjusted under 35 U.S.C. 154(b) by 1218 days.

(21) Appl. No.: 11/105,165

(22) Filed: Apr. 13, 2005

(65) Prior Publication Data

US 2006/0035972 A1      Feb. 16, 2006

Related U.S. Application Data

(60) Provisional application No. 60/601,095, filed on Aug. 12, 2004.

(51) Int. Cl.
*A61K 31/195* (2006.01)
(52) U.S. Cl. ...................................................... 514/561
(58) Field of Classification Search ................ 514/1, 561
See application file for complete search history.

(56) References Cited

U.S. PATENT DOCUMENTS
7,256,002 B2 *  8/2007  Cox et al. ........................ 435/7.1

FOREIGN PATENT DOCUMENTS
GB          2006207 A   *   5/1979

OTHER PUBLICATIONS

Aguado, B., et al., Biochem. J., vol. 341, pp. 679-689,1999.
Angelino, F., et al., Int. J. Clin. Pharmacol. Ther. Toxicol., vol. 23, No. 10, pp. 569-572, 1985.
Balch, Phyllis A., et al, "Prescription For Nutritional Healing, 3rd edition", Avery Publishing, p. 47, New York, 2000.
Barisic N., et al., Croatian Medical Journal, vol. 44, No. 4, pp. 489-493, 2003.
Barrett, G.C., "Amino Acid Derivatives, A Practical Approach", Oxford University Press, 1999.
Brass, E.P., et al., J. Am. Coll. Nutr., vol. 17, No. 3, pp. 207-215, 1998.
Broom, M.F., et al., European Journal of Paediatric Neurology. 5 Suppl A, pp. 33-35, 2001.
Chattopadhyay, S., et al., Human Molecular Genetics. vol. 11, No. 12, pp. 1421-1431, 2002.
Cherchi, A., et al., Int. J. Clin. Pharmacol. Ther. Toxicol., vol. 23, No. 10, pp. 569-572, 1985.
Das, A M., et al., European Journal of Paediatric Neurology, 5 Suppl A, pp. 143-146, 2001.
Davis, A. T., et al., Chromatogr, vol. 306, pp. 79-87, 1984.
De Voer, G., et al., European Journal of Paediatric Neurology, 5 Suppl A, pp. 115-120, 2001.
Doqu, K.oqi, National Kidney Foundation, Am. J. Kidney Dis., vol. 35, No. 6 Suppl 2 S1, p. 140 , 2000.
Dunn, W.A., et al., J.Biol. Chem. vol. 257, pp. 7948-7951, 1982.
Dunn, W.A., et al., J. Biol. Chem. vol. 259, pp. 10764-10770, 1984.
Eriksson, B.O., et al., Eur.J. Pediatr., vol. 147, pp. 662-663, 1988.
"*Escherichia coli* and *Salmonella*", Cellular and Molecular Biology, 2nd Edition, American Society for Microbiology, Washington, D.C., 1996.
Ezaki, J., et al., J Biochem (tokyo) Sep., vol. 128, No. 3, pp. 509,2000.
Ghose, M., et al., Pharm. Res., vol. 8, pp. 771-775, 1009.
Girgis, S., et al., Gene vol. 210, pp. 315-324, 1998.
Gupta, P., et al., P.N.A.S.USA, vol. 98, No. 24, p. 13571, 2001.
Gupta, P., et al., Molecular Psychiatry, vol. 7, pp. 434-436, 2002.
Gupta, P., et al., P.N.A.S. USA., vol. 100, No. 21m, pp. 12325-12330, 2003.
Hagen, TM, et al., Proc. Natl. Acad. Sci.USA., vol. 95, No. 16, pp. 9562-9566,1998.
Vesa, J., et al., Nature, vol. 376, pp. 584-587,1995.
Hellsten, E., et al., Nature vol. 15, pp. 5240-5245, 1996.
Higuchi, T., et al., Prodrugs as Novel Delivery Systems, vol. 14 of the ACS Symposium Series.
Higuchi, T., et al., "Bioreverible Carriers in Drug Design", ed. Edward B. Roche, American Pharmaceutical Association and Pergamon Press, 1987.
Hofmann, S.L., et al., Current Molecular Medicine. vol. 2, No. 5, pp. 423-437, 2002.
Hulse, J.D., et al., Fed. Proc. Fed.Am. Soc.Exp. Biol., vol. 38, p. 676, 1979.
Isosomppi, J., et al., Human Molecular Genetics. vol. 11, No. 8, pp. 885-891, 2002.
Iyer, R.N., et al., J Assoc Physicians India, vol. 8, No. 11, pp. 1050-1052, 2000.
Jones, John, "Amino Acids and Peptide Synthesis", Oxford University Press, 1992.
Kakimoto, Y., et al., J. Biol. Chem. vol. 245, pp. 5751-5758, 1970.
Karpati, G., et al., Neurology, vol. 25, pp. 16-24, 1975.
Katz, M.L., et al., European Journal of Paediatric Neurology. 5 Suppl A, pp. 109-114, 2001.
M.L. Kaz, M.L., Biochem.Biophy. Acta, vol. 1317, pp. 192-198,1996.
Labadie, J., et al., N. N. Biochem. J., vol. 160, pp. 85-95, 1976.
Lam CW., et al., American Journal of Medical Genetics, vol. 99, No. 2, pp. 161-163, 2001.
Lavrov, A.Y., et al., European Journal of Paediatric Neurology, vol. 6, No. 3, pp. 161-164, 2002.
Lehtovirta, Maarit, et al., Human Molecular Genetics,vol. 10, No. 1, 2001.
Lehtovirta, Maarit, et al., Human Molecular Genetics,vol. 10, No. 1, pp. 69-75, 2001.

(Continued)

*Primary Examiner* — Kevin Weddington
(74) *Attorney, Agent, or Firm* — Law Offices of Indu M. Anand

(57) ABSTRACT

The invention provides compositions for and methods of treating a number of disorders. In one embodiment, the invention provides a method of treating a wide range of conditions by administering to a human being in need of such treatment, a therapeutically effective amount of (a) N-6-trimethyl-L-lysine of at least 98% purity, (b) a prodrug thereof, (c) an aliphatic chain derivative thereof, (d) an ester derivative thereof, (e) an amide derivative thereof, or (f) a pharmaceutically acceptable salt of said N-6-trimethyl-L-lysine or said prodrug.

5 Claims, 4 Drawing Sheets

OTHER PUBLICATIONS

Lindblad, B., et al., J. Am. Chem. Soc., vol. 91, pp. 4604-4606, 1969.
Lonnqvist, T., et al., Neurology, vol. 57, No. 8, pp. 1411-1416, 2001.
Mao, Q., et al., FEBS Letters, vol. 555, No. 2, pp. 351-357, 2003.
Martin, J.-J., Dev. Neurosci. vol. 13, pp. 331-338, 1991.
Mitchell, W.A., et al., European Journal of Paediatric Neurology, 5 Suppl A, pp. 121-125, 2001.
Mitchell, W.A., et. al., European Journal of Paediatric Neurology, 5 Suppl A, pp. 21-27, 2001.
Mitchison, H.M., et al., Brain Pathology, vol. 14, No. 1, pp. 86-96, 2004.
Moretti, S., et al., "Effect of L-carnitine on human immunodeficiency virus-1 infection-associated apoptosis", a pilot study, Blood, vol. 91, No. 10, pp. 3817-3824, 1998.
Muller, VJ., et al., European Journal of Paediatric Neurology, 5 Suppl A, pp. 197-201, 2001.
Nijssen, P.C., et al., Movement Disorders, vol. 17, No. 3, pp. 482-487, 2002.
Ninds Batten Disease Information Page at http://www.ninds.nih.gov/disorders/batten/batten.htm.
Nucleic Acids Res. vol. 30, No. 1, p. 59, 2002.
O'Connor, JE, Adv Exp Med Biol., vol. 272, pp. 183-195, 1990.
Ogawa, H., et al., J. Biochem.(Tokyo), vol. 90, pp. 381-390, 1981.
Olson, et al., J. Nutr. vol. 117, No. 6, pp. 1024-1031, 1987.
Persaud-Sawin, D.A., et al., Human Molecular Genetics. vol. II, No. 18, pp. 2129-2142, 2002.
Rakheja D., et al., Biochemical & Biophysical Research Communications, vol. 317, No. 4, pp. 988-991, 2004.
Rebouche, C.J., et al., Biochim. Biophys. Acta, pp. 22-29, 1980.
Sachan, D.S., et al., Biochem, J., vol. 188, pp. 529-534, 1980.
Sandor, A., et al., Clin. Chim. Acta., vol. 176, pp. 17-27, 1988.
Santavuori, P., et al., European Journal of Paediatric Neurology, 5 Suppl A, pp. 157-161, 2001.
Sappington, R.M., et al., Investigative Ophthalmology & Visual Science, vol. 44, No. 9, 3725-3731, 2003.
Savukoski, M., et al., Nat.Genet, vol. 19, pp. 286-288, 1998.
Scholte, H.R., et al., J.Clin. Chem..Clin. Biochem. vol. 28, pp. 351-357, 1990.
Scholte, HR, J Clin Chem Clin Biochem, vol. 28, No. 5, p. 35, May 1990.
Sharp, J.D., et al., Hum. Mol.Genet., vol., 6, pp. 591-595, 1997.
Sharp, J.D., et al., European Journal of Paediatric Neurology. 5 Suppl A, pp. 29-31, 2001.
Siakotos, A.N., et al., European Journal of Paediatric Neurology. 5 Suppl A, pp. 151-156, 2001.
Sleat, D.E., et al., Science, vol. 277, pp. 1802-1805, 1997.
Sondhi, D., et al., Archives of Neurology, vol. 58, No. 11, pp. 1793-1798, 2001.
Stanley, C.A., et al., Ann.Neuro. vol. 30, pp. 709-716, 1991.
Tein, I., J Child Neurol, vol. 17, Suppl No. 3, 3S57-82; discussion 3S82-3, Dec. 2002.
Teixeira, C.A., et al., Human Mutation, vol. 21, No. 5, pp. 502-508, 2003.
Treem, W.R., et al., N.Engl.J.Med, vol. 319, pp. 1331-1336, 1988.
Van Diggelen, O.P., et al., Annals of Neurology, vol. 50, No. 2, pp. 269-272, 2001.
Vaz, Frederic M., et al., Clin. Chem. vol. 48, No. 6, pp. 826-834, 2002.
Vaz, F.M., et al., Biochem.J., vol. 361, pp. 417-429, 2002.
Wang, Y., et al., PRoc. Natl.Acad. Sci. USA vol. 96, pp. 2356-2360, 1999.
Warburton, M.J., et al., FEBS Letters, vol. 500, No. 3, pp. 145-148, 2001.
Weimer, J.M., et al., NeuroMolecular Medicine. vol. 1, No. 2, pp. 111-124, 2002.
Weissman, N., et al. J.Biol.Chem. vol. 140, p. 549, 1943.
Wang, Y., et al., Proc. Natl.Acad. Sci. USA, vol. 96, pp. 2356-2360, 1999.
Winter, S., et al., J. Child Neurol, vol. 10, Supple No. 2, pp. 45-51, 1995.

* cited by examiner

TLC Picture of TML

Spot 1 & 2: TML
Spot 3: Reference

1H NMR (D2O, 300 MHz, full scale)
Proton NMR of TML $^1$H NMR (D$_2$O; 300 MHz, Expanded)
Proton NMR of TML Mass Spectrum of TML
Positive Ion Data

THERAPEUTIC COMPOSITIONS AND USES

PRIOR APPLICATIONS

This application claims priority to provisional application Ser. No. 60/601,095, which was filed on Aug. 12, 2004 and entitled "N-6 trimethyllysine, its derivatives, and formulations as highly effective therapeutic and supplement for treatment of various classes of neuronal ceroid lipofuscinosis (NCL) and other neurodegenerative diseases resulting from defects in carnitine biosynthesis pathway".

INCORPORATION BY REFERENCE

All books, manuals, articles, and papers that are cited herein are hereby incorporated by reference in their entirety.

BACKGROUND

Introduction

Batten Disease is the juvenile form of a group of progressive neurological diseases called neuronal ceroid lipofuscinoses (NCL). Characterized by the accumulation of lipopigment in the brain, as well as in non-neural tissue, these diseases may also be referred to as lipopigment storage disorders.

Four main types of NCL, which differ in age onset and lipopigment accumulation, have been identified. These are:

Infantile (Santavuori disease): Onset before two years of age,

Late-Infantile (Jansky-Bielschowsky): Onset before four years of age,

Juvenile (Batten disease, Speilmeyer-Sjogren disease): Onset before eight years of age, Adult Form (Kuf disease, Parry disease): Onset before forty years of age, Batten disease is named after the British pediatrician who first described it in 1903. It is also known as Spielmeyer-Vogt-Sjogren-Batten disease. The disease progresses and strikes without warning. The first signs of Batten Disease may be visual impairment and seizures. As the disease progresses, visual impairment leads to blindness and myoclonic seizures become more frequent and intense. A child with Batten Disease will also have a marked decline in cognitive function, noticeable personality and behavioral changes, a loss of communication skills, a loss of motor skills, apparent plasticity, facial grimacing and abnormal body movements. Thus Batten Disease leads to a vegetative state and is ultimately fatal (NINDS Batten Disease Information Page at http://www.ninds.nih.gov/disorders/batten/batten.htm, attached hereto as Appendix A).

Neuronal ceroid-lipofuscinosis are a group of inherited progressive neurometabolic diseases, previously considered as several separate syndromic entities, with considerable variability in clinical, pathological manifestations, and genetic findings. All diseases in this group are characterized by abnormal storage of the autofluorescent proteolipopigments in neuronal and other formulas with an average incidence estimated at 1:5/100,000. Abnormal proteins occur in the lysosomes, due to defects in lysosomal proteases or related enzymes or in other words, defective lysosomal proteolysis. Abnormal accumulation of proteins in various tissues is not only responsible for the Batten disease, but it is also well known that it is responsible for other well known disorders, such as Alzheimer's disease, Parkinson's disease, Lewy body dementia, Huntington disease. In all these diseases, including Batten disease, undegraded proteins cause loss of neuronal cells.

At genetic level, the neuronal ceroid lipofuscinoses (NCL's) results from mutation in at least eight genes, and these mutations are responsible for causing NCLs, which are a group of neurodegenerative diseases. A summary background of each of these is outlined in the subsequent paragraphs.

NCLs are also classified on the basis of specific gene association and genetic features of the disease, age of onset, clinical manifestations, and pathological changes. The common characteristics in all these disorders is accumulation of autofluorescent storage material in all tissues, but more pronounced in central nervous system. They are listed sequentially.

Neuronal ceroid-lipofuscinosis type 1 (CLN-1) Synonyms: Hagberg-Santavuori disease, Haltia-Santavuori disease, Santavuori disease, and several other synonyms. It is characterized by rapid deterioration with psychomotor retardation, loss of speech, seizures, ataxia, blindness, hypotonia, microcephaly, and occasional convulsions. Mapped to chromosome 1p32. The gene is known to be responsible for the making of palmitoyl-protein thioesterase. It is transmitted as an autosomal recessive trait. J. Vesa, E. Hellsten, L. A. Verkruyse, L. A. Camp, J. Rapola, P. Santavuori, S. L. Hofmann, L. Peltonen, Nature 376, 584-587, 1995, E. Hellsten, J. Vesa, V. M. Olkkonen, A. Jalanko, L. Peltonen, EMBO J., 15, 5240-5245, 1996.

Neuronal ceroid-lipofuscinosis type 2 (CLN-2) Synonyms: Bernheimer-Seitelberger syndrome, Bielschowsky amaurotic idiocy, Bielschowsky disease, Jansky-Bielschowsky disease, Seitelberger disease, late infantile amaurotic idiocy, late infantile Batten disease, late infantile neuronal lipofuscinosis (LINCL), subacute late infantile neuronal ceroid-lipofuscinosis. This is the second most common variant with a subacute course after onset in infancy or early childhood characterized by refractive epilepsy, mental regression, ataxia, visual loss, and progressive deterioration. Mapped to chromosome 11p15. The CLN-2, the classical late infantile neuronal ceroid lipofuscinosis has been associated with mutation in a lysosomal protein. D. E. Sleat, R. J. Donnelly, H. Lackland, C.-G. liu, I. Sohar, R. K. Pullarkat and P. Lobel, Science 277, 1802-1805, 1997.

Two novel CLN2 gene mutations in a Chinese patient with classical late-infantile neuronal ceroid lipofuscinosis have been discovered (Lam C W., Poon, P. M., Tong S F., Ko C H., American Journal of Medical Genetics. 99(2): 161-3, 2001). It was shown that the R208X mutation in CLN2 gene is associated with reduced cerebrospinal fluid, pterins in a girl with classic late infantile neuronal ceroid lipofuscinosis (Barisic N., Logan P., Pikija S., Skarpa D., Blau N., Croatian Medical Journal. 44(4):489-93, 2003).

Neuronal ceroid-lipofuscinosis type 3 (CLN-3) Synonyms: Batten syndrome (BTS) Batten-Mayou syndrome, Batten-Spielmeyer-Vogt disease, Spielmeyer-Sjögren syndrome, Spielmeyer-Vogt-Batten disease, Spielmeyer-Vogt-Sjögren disease, Stock-Spielmeyer-Vogt syndrome, Vogt-Spielmeyer disease, chronic juvenile neuronal ceroid-lipofuscinosis (JNCL), juvenile amaurotic family idiocy, juvenile amaurotic idiocy, juvenile Batten disease, juvenile cerebrorenal degeneration, juvenile neuronal lipofuscinosis (JNCL), juvenile onset neuronal ceroid-lipofuscinosis, and pigmentary retinal neuronal heredodegeneration. The most commonly occurring variant has a chronic course after juvenile onset with an estimated incidence of 1:25,000. The first symptom is usually visual failure, which takes place between the ages of 4 and 15 years. The early symptoms are followed by epilepsy and progressive physical and mental deterioration. Batten disease gene maps to chromosome 16p12.1.56. Further it has been shown that the Batten disease protein CLN3P localizes into membrane lipid raits, which are detergent-resistant membranes (Rakheja D., Narayan S. B., Pastor J. V., Bennett M. J., Biochemical & Biophysical Research Communications. 317(4):988-991, 2004. Studies have been carried out on the intracellular trafficking of CLN3 protein, underlying the childhood neurodegenerative conditions of Batten disease (Mao Q., Xia H., Davidson B. L., FEBS Letters. 555(2):351-7, 2003).

Genetic structures of the genes involved in NCL have been studied and the genomic structures of three CLN3-like genes in Caenorhabditis elegans has been determined (Mitchell, W. A., Porter, M., Kuwabara, P., Mole, S. E., European Journal of Paediatric Neurology, 5 Suppl A: 121-5, 2001). The mutated form of the Caenorhabditis elegans homologues CLN3 gene has been studied and studies have been directed towards the structural elucidation in juvenile neuronal ceroid lipofuscinosis (De Voer G., Jansen G., van Omen G. J., Peters D. J., Taschner, P. E., European Journal of Paediatric Neurology, 5 Suppl A: 115-20, 2001). Similarly Mouse gene knockout models for the CLN2 and CLN3 forms of ceroid lipofuscinosis have been analyzed Katz M. L., Johnson G. S., European Journal of Paediatric Neurology. 5 Suppl A: 109-14, 2001).

Neuronal ceroid-lipofuscinosis type 4 (CLN-4) Synonyms: Kufs disease, Kufs-Mayer disease, adult amaurotic idiocy, adult ceroid lipofuscinosis, adult ganglioside lipidosis, adult neuronal ceroid-lipofuscinosis, adult recessive neuronal ceroid lipofuscinosis, chronic adult-recessive neuronal ceroid-lipofuscinosis, late familial amaurotic idiocy late ganglioside lipidosis. A rare variant with onset of symptoms between the ages of 20 and 50 years with a chronic course and associated with cerebellar ataxia, bulbar symptoms, and extrapyramidal and pyramidal signs, but without retinal lesions and rapidly progressive dementia. Transmitted as an autosomal recessive trait but some cases are sporadic. J.-J. Martin, Dev. Neurosci. 13,331-338, 1991.

Neuronal ceroid-lipofuscinosis type 5 (CLN-5) Synonyms: Boehme disease, Parry neuronal ceroid-lipofuscinosis, adult dominant neuronal ceroid-lipofuscinosis, chronic adult dominant neuronal ceroid-lipofuscinosis, dominant Kufs disease, and dominant neuronal ceroid-lipofuscinosis. It is a cerebellar syndrome with onset early in the fourth decade, characterized by epileptic fits, myoclonic epilepsy, progressive dementia, and hypertension. CLN5 has been shown to be a novel gene encoding a transmembrane protein which is mutated in Finnish variant of LINCL. M. Savukoski, T. Klockars, V. Holmberg, P. Santavuori, E. S. Lander, L. Peltonen, Nat. Genet. 19, 286-288, 1998.

Neuronal ceroid-lipofuscinosis type 6 (CLN-6) Synonyms: Zeman-Dyken-Lake-Santavuori-Savukoski disease, and subacute transitional early juvenile neuronal ceroid-lipofuscinosis. A subacute variant with onset in late childhood or in early period with seizures, ataxia, retinal lesions, mental failure, and gradual neurological deterioration. Novel mutations in the CLN6 gene caused a variant, late infantile neuronal ceroid lipofuscinosis (Teixeira C. A., Espinola J., Huo L., Kohischutter J., Persaud Sawin D. A., Minassian B., Bessa C. J., Guimaraes, A., Stephan D. A., Sa Miranda M. C., MacDonald M. E., Ribeiro M. G., Boustany R. M., Human Mutation. 21(5):502-8, 2003). Fine mapping of bovine ceroid lipofuscinosis was confirmed by orthology with CLN6 (Broom M. F., Zhou C., European Journal of Paediatric Neurology. 5 Suppl A:33-5, 2001). Analysis of candidate genes in the CLN6 critical region was also carried out using in silico cloning (Sharp J. D., Wheeler R. B., Schultz R. A., Joslin J. M., Mole S. E., Williams R. E., Gardiner R. M., European Journal of Paediatric Neurology. 5 Suppl A: 29-31, 2001). The loci for classical and late infantile neuronal ceroid lipofuscinosia have been shown to map to chromosomes 11p15 and 15q21-23 (J. D. Sharp, R. B. Wheeler, M. Savukoski, I. E. Jarvela, I. Peltonen, R. M. Gardiner, R. E. Williams, Hum. Mol. Genet., 6,591-595, 1997.

Neuronal ceroid-lipofuscinosis type 7 (NCL-7), a group of previously unclassified atypical forms of NCL, representing about 12 to 20% of those afflicted, is characterized by accumulation of ceroid-lipofuscin in the secondary lysosomes or neurons and cells of other tissues, such as skin, conjunctiva, and lymphocytes. It has been shown that the Turkish variant late infantile neuronal ceroid lipofuscinosis (CLN7) may be allelic to CLN8 (Mitchell W. A., Wheeler R. B., Sharp J. D., Bate S. L., Gardiner R. M., Ranta, U. S., Lonka L., Williams R. E., Lehesjoki, A. E., Mole S. E., European Journal of Paediatric Neurology, 5 Suppl A:21-7, 2001).

It has been shown that there is specific accumulation of a hydrophobic protein, subunit c of ATP synthase, in lysosomes from the cells of patients with the late infantile form of NCL (LINCL), and that this is caused by a defect in the CLN2 gene product, tripeptidyl peptidase I (TPP-I). The data by the authors show that TPP-I is involved in the initial degradation of subunit c in lysosomes and suggests that its absence leads directly to the lysosomal accumulation of subunit c. (Ezaki, J., Takeda-Ezaki, M., Kominami, E., J Biochem (tokyo) September, 128(3), 509, 2000).

Background of the Key Enzymes and Proteins Involved in the Manifestation of the NCL Conditions are Outlined in Subsequent Paragraphs.

The polypeptidase enzymes, palmitoyl protein thioesterase 1 (PPT1) and palmitoyl protein thioesterase 2 (PPT2) catalyze the hydrolysis of long chain fatty acids acyl coenzymes. Further PPT1 hydrolyzes fatty acids from modified cysteine residues in proteins that are undergoing degradation in lysosomes. PPT1 deficiency is associated with infantile neuronal ceroid lipofuscinosis (INCL) or infantile Batten disease. The deficiency of PPT1 has been clearly shown to be associated with NCL in the case of mice (P. Gupta, A. A. Soyombo, A. Atashband, K. E. Wisniewski, J. M., Shelton, J. A. Richardson, R. E. Hammer, S. L. Hofmann, P.N.A.S. USA, 98 (24), 13571, 2001). A case of first adult neuronal ceroid lipofuscinosis was found to be associated with the palmitoyl-protein thioesterase deficiency (van Diggelen O. P., Thobois S., Tilikete C., Zabot M. T., Keulemans J. L., van Bunderen P. A., Taschner P. E., Losekoot M., Voznyi Y. V., Annals of Neurology, 50(2): 269-72, 2001). Both the enzymes, PPT1 and PPT2 are responsible for hydrolyzing long chain fatty acyl CoAs with a similar fatty acid optimum chain length of 14-18 carbon atoms. Although PPT2 hydrolyzes very long chain fatty acids more efficiently than PPT1 (Aguado, B., and Campbell, R. D., Biochem. J., 341, 679-689, 1999).

The palmitoyl protein thioesterase-2 (PPT2) gene encodes a lysosomal thioesterase homologous to PPT1. It has been shown that PPT2 deficiency in mice causes an unusual form of neuronal ceroid lipofuscinosis with striking visceral manifestations. In the study cited above (P. Gupta et al., 2001) all PPT2-deficient mice displayed a neurodegenerative phenotype with spasticity and ataxia by 15 months. The bone marrow of such mice was infiltrated by brightly autofluorescent macrophages and multinucleated giant cells. PPT2 deficiency in mice manifests as a neurodegenerative disorder with visceral features. Although PPT2 deficiency has not been described in humans, manifestations would be predicted to include neurodegeneration with bone marrow histiocytosis, visceromegaly, brown pancreas, and linkage to chromosome 6p21.3 in affected families (P. Gupta, A. A. Sombo, J. M. Shelton, I. G. Wilkofsky, K. E. Wisniewski, J. A. Richardson, and S. L. Hofmann, P.N.A.S. USA., 100 (21): 12325-12330, 2003).

Further it has been shown that deficiency of palmitoyl protein thioesterase (PPT) which leads to the neurodegenerative disease especially the infantile neuronal ceroid lipofuscinosis (INCL), is characterized by an almost complete loss of cortical neurons. PPT expressed in COS-1 cells is recognized by mannose-6-phosphate receptor (M6PR) and is routed to lysosome, but a substantial fraction of PPT by confocal microscopy, cryoimmunoelectron microscopy and cell fractionation. In mouse primary neurons and brain tissue, PPT is localized in synaptosomes and synaptic vesicles but not in lysosomes. (Maarit Lehtovirta, Aija Kyttala, Eeva-Liisa Eskelinen, Michael Hess, Outi Heinonen and Anu Jalanko, Human Molecular Genetics, Vol 10, No 1 2001).

Occurrence of L-Carnitine:

The original discovery of L-carnitine occurred in 1905 when Gulewitsch and Krimberg found the substance in muscle tissue. Subsequently, the formula of carnitine was shown to be L-b-hydroxy-g-n-trimethylaminobutyric acid. It is a derivative of the amino acid lysine, and was first isolated from meat (carnus) in 1905, since L-carnitine appeared to act as a vitamin in the mealworm (Tenebrio molitor).

Human requirements for L-carnitine are usually met with a combination of diet and endogenous biosynthesis. The primary dietary sources of L-carnitine are meat, poultry, fish, and dairy products, while in comparison, vegetable products provide fairly small amounts. Dietary L-carnitine appears to be rapidly absorbed from the intestinal lumen across the mucosal membrane by both passive and active transport mechanisms. This carnitine is then taken up from the portal circulation by the liver and subsequently released into the systemic circulation.

Diagnosis of Batten Disease and NCL:

An Australasian diagnostic service for the neuronal ceroid lipofuscinoses (Muller V J. Paton B C. Fietz M J., European Journal of Paediatric Neurology, 5 Suppl A: 197-201, 2001) has compiled the diagnostic methods available for these neurodegenerative diseases. The method for pre- and postnatal diagnosis of patients with the CLN1 and CLN2 conditions is an assay of palmitoyl-protein thioesterase and tripeptidyl peptidase I activities, and the authors have been able to indicate the progression of the diseases. A review of various clinical and neuroradiological aspects of NCL disorders has been carried out (Santavuori P., Vanhanen, S. L., European Journal of Paediatric Neurology, 5 Suppl A: 157-61, 2001). Altered levels of high-energy phosphate compounds have been observed in fibroblasts in different forms of neuronal ceroid lipofuscinoses. This shows evidence for mitochondrial involvement (Das, A M., von Harlem, R. Feist, M., Lucke, T., Kohlschutter, A., European Journal of Paediatric Neurology, 5 Suppl A: 143-6, 2001).

NCL Phenotype

The first three Russian cases of classical late-infantile neuronal ceroid lipofuscinosis have been reported (Lavrov, A. Y., Ilyna, E. S., Zakharova, E. Y., Boukina, A. M., Tishkanina, S. V., European Journal of Paediatric Neurology. 6(3): 161-4, 2002). There are also several possible subtypes—protracted, atypical, and earlier or later onset, which have similar clinical symptoms and may become apparent at different ages and progress at different rates. Ultimately, all forms are fatal. In the US, the incidence of all four types may be as high as two or three per 100,000 births. Batten disease is a fatal, inherited disorder of the nervous system that begins in childhood. "Late infantile neuronal ceroid lipofuscinosis (LINCL) is an autonomic excessive neurodegenerative disease caused by mutations in the CLN2 gene (NINDS Batten Disease Information Page at http://www.ninds.nih.gov/disorders/batten/batten.htm attached hereto as Appendix A). CLN2 encodes a lysosomal protease that was later found to be identical with lysosomal tripeptidyl peptidase. The specificity of lysosomal tripeptidyl peptidase-1 was determined by its action on angiotensin-II analogues (Warburton M. J., Bernardini F., FEBS Letters, 500(3): 145-8, 2001). It has been shown that the enzyme Palmitoyl protein thioesterase (PPT) localizes into synaptosomes and synaptic vesicles in neurons, and its implications for infantile neuronal ceroid lipofuscinosis (INCL) have been postulated (Lehtovirta, M., Kyttala, A., Eskelinen, E. L., Hess, M., Heinonen, O., Jalanko, A., Human Molecular Genetics. 10 (1):69-75, 2001). An excellent review on the selectivity and types of cell death in the neuronal ceroid lipofuscinoses has been written (Mitchison H. M., Lim M. J., Cooper J. D., Brain Pathology, 14 (1):86-96, 2004). It was shown that optic nerve degeneration takes place in a murine model of juvenile ceroid lipofuscinosis (Sappington R. M., Pearce D. A., Calkins D. J., Investigative Ophthalmology & Visual Science. 44(9):3725-31, 2003). At the cellular level, LINCL is characterized by lysosomal accumulation of autoflourescent storage material whose major identifiable component is mitochondria ATP synthase subunit c (subunit c) in neurons and other cell types. Affected individuals usually develop normally until about age 3 years, at which point they exhibit symptoms such as ataxia and seizure. The disease is associated with progressive loss of neurons and photoreceptors, and, within several years (NINDS; Batten Disease Information Page.). LINCL patients become blind, mute, bedridden and demented. Currently, there is no effective treatment for the disease and death typically occurs between age 6 and 15. Early symptoms of this disorder usually appear between the ages of 2 and 4, when parents or physicians may notice a previously normal child who has begun to develop vision problems or seizures (NINDS Batten Disease Information Page). In some cases the early signs are subtle, taking the form of personality and behavior changes, slow learning, clumsiness, or stumbling. Over time, affected children suffer mental impairment, worsening seizures, and progressive loss of sight and motor skills. Eventually, children with Batten disease become blind, bedridden, and demented, and the disease subsequently becomes fatal (NINDS Batten Disease Information Page).

Present Approaches Towards Treatment of NCL

Present Approaches Towards Treatment of NCL:

a. Feasibility of gene therapy for late neuronal ceroid lipofuscinosis has been proposed (Sondhi D., Hackett N. R., Apblett, R. L., Kaminsky S. M., Pergolizzi, R. G., Crystal R. G., Archives of Neurology. 58(11): 1793-8, 2001).

b. Additionally, hematopoietic stem cell transplantation in infantile neuronal ceroid lipofuscinosis has been proposed (Lonnqvist T., Vanhanen S. L., Vettenranta K., Autti T., Rapola J., Santavuori P., Saarinen-Pihkala U. M. (Neurology. 57(8): 1411-6, 2001).

c. Assessment of dietary therapies in a canine model of Batten disease has been carried out (Siakotos A. N., Hutchins G. D., Farlow M. R., Katz M. L., European Journal of Paediatric Neurology. 5 Suppl A: 151-6, 2001).

However, NCLs are generally fatal. Thus, there is a need for treatment for Batten disease and many of the other diseases mentioned above for which no effective treatment is available.

SUMMARY

In one embodiment, the invention provides a method of administering any of the following to a human being in need thereof: (a) N-6-trimethyl-L-lysine, (b) a prodrug thereof, or (c) a pharmaceutically acceptable salt of said N-6-trimethyl- L-lysine or said prodrug, said administered therapeutic being at least 98% pure. It is believed that these can be used to treat a human being diagnosed with one or more of the following: defects in carnitine biosynthesis pathway, efficiency of endogeneous TML, over-accumulation of TML bound protein at the cellular level, renal failure conditions, hyperammonemic Encepalophathy, over-accumulation of glutamine in the brain, reduced and deficient fatty acid metabolism and shuttling of fatty acid in to mitochondria, insufficient ATP production or subsequent energy production and all the cellular activities associated with this events, defective fatty acid oxidation resulting from carnitine deficiency, hypoglycemia, hypoketotic, encephalopathy, reye-like syndrome, for recurrent seizures and developmental delay, AIDS or AIDS-like conditions, over-accumulation of lipids causing myopathy, myoglobinuria, neuropathy, cardiomyopathy, ammonia overproduction, hyperammonemic syndromes, over accumulation of triacylglycrols, Batten diseases, infantile neuronal lipofuscinoses diseases (Santavvori diseases), Late infantile neuronal lipofuscinoses diseases (Jansky-Bielscowsky), Speilmeyer disease, Sjorgsen disease, Kuf diseases, Parry diseases, Juvenile or adult neuronal lipofuscinoses diseases ("NCL") disease, lysosomal accumulation of mitochondrial ATP synthase subunit and their by products, Ataxia and Seizures, various stages of mental impairment, (e.g., learning disability, clumsiness, stumbling, impaired motor skills, and dementia, hyperandrogenism caused by NCL, defective dopamine receptors caused by NCL, epileptic fits, myoclonic epilepsy, Parkinson's disease, and Alzheimer's disease. Preferably, the disease being treated is an NCL. Most preferably, it is Late Infantile Neuronal Ceroid Lipofuscinosis.

In another embodiment, the invention provides a compound represented by Formula 1

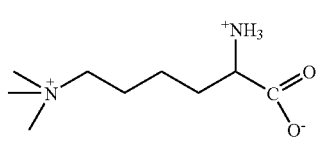

Formula 1 that is at least 98% pure.

Further provided is a compound represented by Formula II:

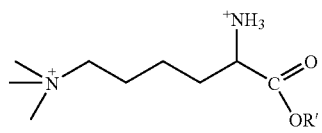

(Formula II)

wherein R' is selected from an alkyl having between 1 and 5 carbon atoms, and an aromatic ring.

In another embodiment, the invention provides a compound represented by Formula III:

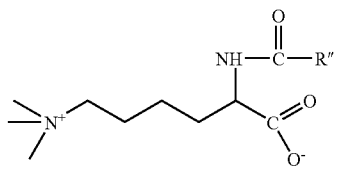

Formula III wherein R" is selected from an alkyl having between 1 and 5 carbon atoms.

Further provided is a compound represented by Formula IV:

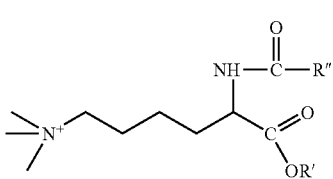

Formula IV wherein R' is selected from an alkyl having between 1 and 5 carbon atoms, and
wherein R" is selected from an alkyl having between 1 and 5 carbon atoms.

In yet another embodiment, the invention provides a compound represented by Formula V:

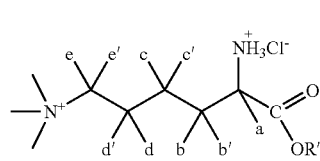

(Formula V)

wherein a, a', b, b'; c, c', d, d', e, and e' are independently selected from H, deuterium, and an alkyl having between 1 and 5 carbon atoms. R' is H, an alkyl having 1-5 carbon atoms or an aromatic ring. In a preferred embodiment, at least one of the nitrogens is nitrogen 15.

The invention further provides a method of synthesizing a compound represented by formula II

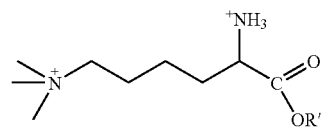

Formula II wherein R' is selected from the group consisting of an alkyl having between 1 and 5 carbon atoms and an aromatic ring, including contacting a compound of formula I

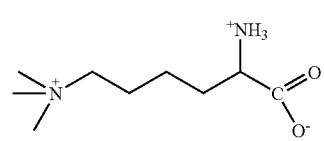

Formula I with excess R'—OH in the presence of acid wherein R' is an alkyl having between 1 and 5 carbon atoms or an aromatic ring.

Further provided is a process for synthesizing a compound represented by formula IV:

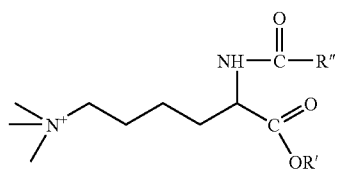

wherein R" is an alkyl having between 1 and 5 carbon atoms, or CF3 and R' is an alkyl having between 1 and 5 carbon atoms or an aromatic ring,
including contacting a compound represented by formula II

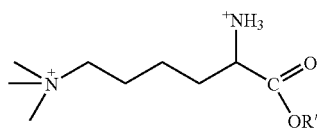

Formula II with R"—COCl in the presence of a mild base, wherein R" is an alkyl having between 1 and 5 carbon atoms or CF3, and R' is an alkyl having between 1 and 5 carbon atoms or an aromatic ring.

Further provided is a process for synthesizing a compound represented by formula III

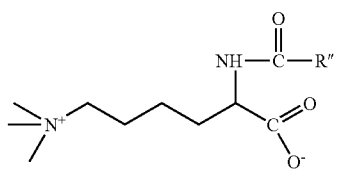

Formula III where R" is an alkyl having 1 to 5 carbon atoms or CF3, involving contacting a compound represented by formula I

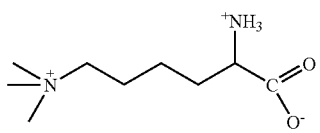

Formula I with either excess R"CO—Cl or excess R"—CO—O—CO—R" in the presence of a mild base.

In yet another embodiment, the invention provides a process for the synthesis of a compound represented by formula VI:

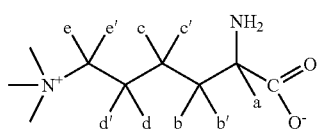

Formula VI involving contacting a compound having formula VII:

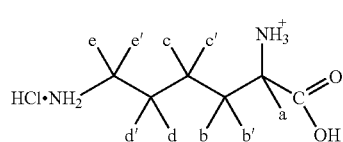

(Formula VII)

with dimethylsulfate and copper carbonate
wherein the a, b, b', c, c', d, d', e, and e' are independently selected from H, deuterium, and an alkyl having from 1 to 5 carbon atoms, and each N is independently selected from nitrogen and N15 labelled nitrogen.

In another embodiment, a process is provided for synthesizing a compound represented by formula V:

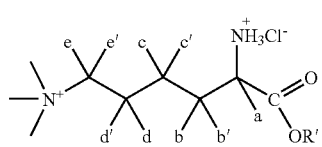

Formula V involving contacting a compound represented by formula VI

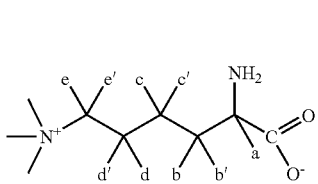

Formula VI with excess R'—OH in the presence of a mild base;
wherein R' is an alkyl having 1-5 carbon atoms or an aromatic ring.

Further provided is a method of purifying a TML compound represented by formula I

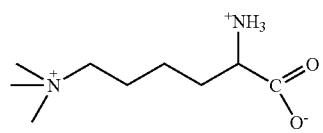

Formula I to at least 98% purity, involving the following steps:
running the TML compound through an ion exchange resin column;
washing the ion exchange resin column with at least 4 times the volume of water as the amount of present TML compound;
eluting the washed TML compound from the ion exchange resin column to obtain eluted TML; and
triturating the eluted TML.
In a preferred embodiment, the process further involves:
dissolving the triturated TML into a polar solvent;
filtering the dissolved TML through a microglass membrane filter; and
lyophilizing the filtered TML at room temperature.

FIGURES

FIG. 1 is a tic picture of TML (lanes 1 and 2) that was synthesized according to Example 1, and a reference of TML (Sigma-Aldrich, St. Louis, Mo.) as a reference in lane 3.

DESCRIPTION

Figure 1:
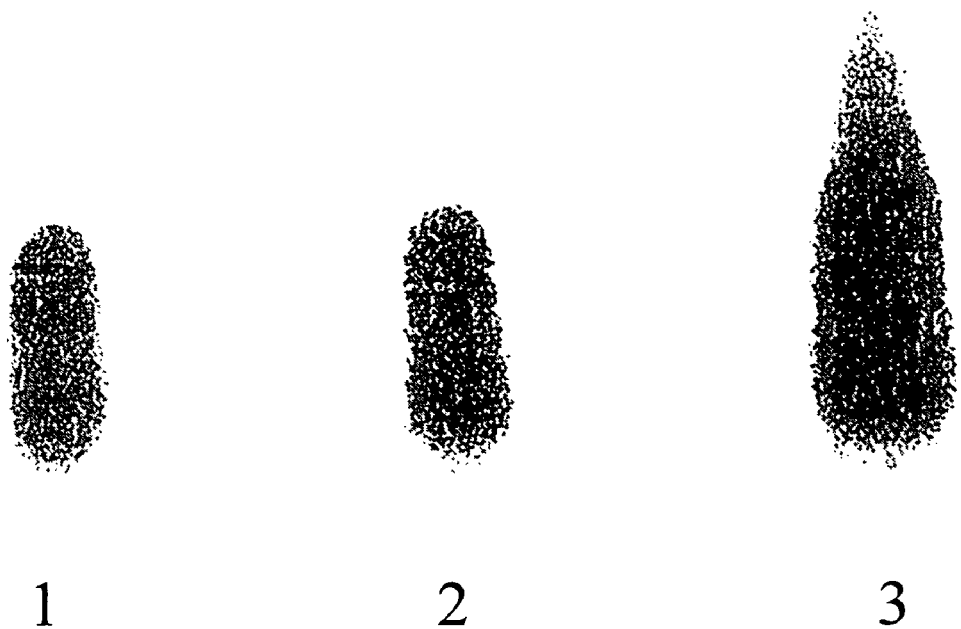

The symbol "-" represents a covalent bond.
Reference to a chain, such as an alkyl, can mean either the branched or unbranched chain unless otherwise noted. An "alkyl", as used herein, means either a branched or unbranched alkyl chain, and includes, for example, methyl, ethyl, n-propyl, isopropyl, n-butyl, sec-butyl, isobutyl, tert-butyl, n-pentyl, and the like.

As used herein, "dilute" means ten percent or less in solution.

As used herein "excess" means a stoicheometry greater than 1:1.

A "mild base", as used herein, means a dilute base.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug or supplement precursor which, following administration, releases the drug or supplement in vivo via a chemical or physiological process (e.g., upon being brought to physiological pH or through enzyme activity). A discussion of the synthesis and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "treat" means to ameliorate or prevent at least one symptom of a disease or a condition.

As used herein, a "salt" can be an internal salt or an external salt. In internal salt, the carboxylic group (which is negatively charged) and the trimethyl group (which is positively charged) form an internal salt. The alpha amino group picks up the proton from the ionized carboxylic group when there is no external salt. In other embodiments, the proton from the ionized carboxylic group is picked up by one or more counterions (i.e., external molecule, atom, or group of atoms) thus forming the external salt. Sometimes, the counter ions can aggregate to include multiple ions. A typical example will be a molecule of water. These are generally multiple molecules and not a single molecule of water attached to a single ion.

Usually, the compound will include one or more different counterions (usually one for each of the two cationic sites in the molecules). The counter ions could be HO⁻, halides, sulfhydryl, carboxylic, phosphines, amines, organic anions, inorganic anions, or a mixture of organic and inorganic anions. These are well known to the skilled artisan. In some cases, there may only be one type of counter ion since internal zwitterions could leave only a single cationic site for salt formation.

Thus, the invention is based on the inventors' realization that certain diseases could be treated with TML or a TML esters (as described below).

Thus, the invention provides a compound represented by formula 1 and having at least 98% purity:

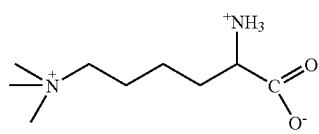

Formula I and preparations, prodrugs, formulations, and encapsulated forms thereof. This compounds are referred to as N-6-trimethyl-L-lysine or "TML". The CAS number for this compound is 23284-33-5.

The skilled artisan will further understand that the above compound (Formula 1) and well as compounds represented by Formulas II-VII are charged and thus have an internal salt or an external salt. External salts require one or more counterions. Each of these compounds may thus further include different counterions (usually one for each of the two cationic sites in the molecules). The counter ions could be HO⁻, halides, sulfhydryl, carboxylic, phosphines, amines, organic anions, inorganic anions, or a mixture of organic and inorganic anions, or other well known counterions In some cases, there may only be one type of counter ion since internal zwitterions could leave only a single cationic site for salt formation.

In yet another embodiment, there may be no counterions because there is an internal salt.

The invention thus provides compounds represented by Formula II:

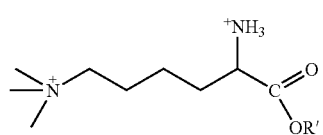

Formula II wherein R' is selected from an alkyl having between 1 and 5 carbon atoms.

It also provides compounds represented by Formula III:

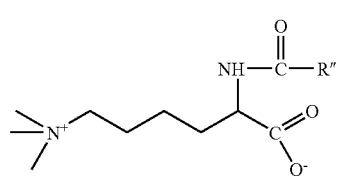

Formula III

Referring to Formula III, R" is selected from an alkyl having between 1 and 5 carbon atoms, and an aromatic ring.

Compounds represented by Formula IV are also provided:

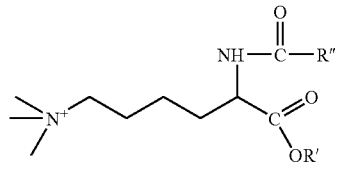

Formula IV

R' is selected from an alkyl having between 1 and 5 carbon atoms, and CF3
and
R" is selected from an alkyl having between 1 and 5 carbon atoms, and an aromatic ring.

The invention further provides compounds represented by Formula V:

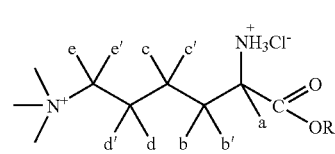

Formula V

R' is selected from H, an alkyl having between 1 and 5 carbon atoms, and a, a', b, b'; c, c', d, d', e, and e' are independently selected from H, deuterium, and an alkyl having between 1 and 5 carbon atoms.

It should be noted that administration of deuterium labeled TML considerably increases unlabelled carnitine and butyrobetain excretion (Vaz and Wanders, J. Biochem., 361-417-429, 2002).

In a preferred embodiment, each N is independently selected from nitrogen or N15 labelled nitrogen.

Referring to formulas II, III, IV, V, VI, and VII, the R', R'', and amino acyl groups are expected to hydrolyze inside the cellular media with one or more intracellular esterases to release free TML from formulas such as II, III, IV and V, VI and VII. Intracellular esterases are known to hydrolyze esters (Ghose, M. and Mitra, A. K., Pharm. Res., 8, 771-775, 1009).

In another embodiment, the invention includes formulations or encapsulations of the compounds shown in Formulas I-VII for efficient intracellular delivery and as a prodrug of TML to proceed to make endogeneous L-carnitine, and to participate in various metabolic activities in the intermediate steps of L-carnitine biosynthesis pathway. These may be used for better adsorption of modified TML into various tissues such as kidney, liver and brain. The R', R'', and aminoacyl groups are expected to hydrolyze inside the cellular media with one or more intracellular esterases to release free TML. Intracellular esterases are known to hydrolyze esters (Ghose, M. and Mitra, A. K., Pharm. Res., 8, 771-775, 1009).

Compounds having one of formulas I, II, III, IV, V, VI or VII are further provided in a physiologically acceptable carrier. These include various solvents, dispersion media, coatings, antibacterial and antifungal agents, isotonic and absorption delaying agents and like. The use of such media and agents for pharmaceutically active substances is well known in the art. Except in so far as any conventional media or agent is incompatible with the active ingredient, its use in the therapeutic and supplement compositions is contemplated. Supplementary active ingredients can also be incorporated into the compositions.

These pharmaceutical and supplement formulations can be used to practice yet another embodiment of the invention, namely, a method of treatment of the afflicted diseases or disorders and conditions resulting from the TML deficiency and imbalance in the endogenous L-carnitine biosynthesis pathway. The method is to be in amount sufficient to exert the biochemical response and increase the conditions towards normalization.

The effective dosages of the TML or its derivatives as outlined in the claims above, and mode of administration in the treatment or improvement of conditions of various disorders can be determined by routine experimentation. The pharmaceutical or supplementation forms suitable for injectable use, or oral use, include sterile aqueous solutions or dispersions and sterile powders for the extemporaneous preparation of sterile injectable solutions or dispersions or oral formulations. In all cases the form must be sterile. It must be stable under the conditions of manufacture and storage and may be prepared against the contaminating effects and actions of microorganisms, such as bacterial and fungi. The carrier can be solvent or dispersion medium. The prevention of the action of microorganisms can be brought about by various antibacterial and antifungal agents. Prolonged absorption of the injectable or oral form can be brought about by the use of the compositions of agents delaying absorption.

TML and its derivatives, due to their charged nature, in the carrier may be administered by any useful route including intravenous, intraperitoneal injection, intranasal, rectal, oral, transdermal or subcutaneous administration. Sterile injectable solutions are prepared by incorporating the TML or its derivatives in the required amount in the appropriate solvent, followed by sterilization.

The compounds of formulas I, II, III, IV, V, VI or VII may be administered to a human being at dosage levels in the range of from about 0.1 mg to about 3,000 mg per day. For example, for a normal adult human having a body mass of about 70 kg, a dosage in the range of from about 0.01 mg to about 100 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular human subject is within the ability of one of ordinary skill in the art having benefit of the instant disclosure.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, acetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

In one embodiment of the invention, any of the compounds of formula I, II, III IV, V, VI, or VII is administered to a human being along with supplementation for one or more co-factors required for TML biosynthesis. It is believed that the necessary co-factors are generally ingested through a normal diet or synthesized in vivo.

In another embodiment of the invention, any of the compounds of formula I, II, III IV, V, VI, or VII is administered to a human being along with supplementation for one or more co-factors required for the hydroxylation of N6-trimethyl-L-lysine by TML dioxygenase. These co-factors are: 2-oxoglutarate (alpha keto glutarate), $Fe^{2+}$, and ascorbate. Substitutes have also been found to be effective. For example, reducing agents such as dithiothreitol can take the place of ascorbate. Vaz and Wanders, (Biochem J. (2002) 361, 417-429). Molecular oxygen is also a co-factor but is not required since a human being would breathe it in. Preferably, the one or more co-factors is given to the human being in an amount that is in excess of the molar equivalent of the TML or TML derivative administered to the human being. Calcium ion was found to cause significant enhancement in the conversion of TML to HTML (D. S. Sachan, C. L. Hoppel, Biochem. J., 188, 529-534, 1980). Thus, in a preferred embodiment, calcium ion supplementation is further administered to the human being, most preferably in an amount that is in excess of the molar equivalent of the given TML.

The compounds of formula (I), (II), (III), (IV), (V), (VI) and (VII) may be prepared according to the exemplary synthetic routes disclosed herein as well as by other conventional organic preparative methods. It is to be understood that the method disclosed are for purposes of exemplifying the instant invention, and are not to be construed in any manner as a limitation thereon.

Examples

1. Improved Method of Synthesis and Production of TML

Starting Raw Material: L-Lysine HCl (Sigma-Aldrich, St. Louis, Mo.), dimethylsulfate (99.99%) (Sigma-Aldrich, St. Louis, Mo.), alkaline copper carbonate (Sigma-Aldrich, St. Louis, Mo.), double distilled water (highly purified), Whatman 3MM Chromotograpy blotting paper (Whatman Inc., Florham Park, N.J.), NaOH (99%+) (Sigma-Aldrich, St. Louis, Mo.), Dowex 50WX8 from (The Dow Chemical Company, Midland Mich.).

Method: L-lysine-HCL (50 gm; 0.274 mol)) was dissolved in distilled water (500 ml), Copper Carbonate basic 72 gm (0.326 mol), was added and the mixture was boiled at 85 Centigrade for 10 minutes. The reaction mixture was cooled to room temperature and filtered with Whatman 3MM paper. The clear filtrate was mixed with dimethylsulfate, 100 ml (1.055 mol) at room temperature, after which 325 ml of aq. sodiumhydroxide solution (10% aq.; 1.055 mol; w/v, in dd water) was added dropwise during 30 minutes, then stirred at room temperature for 60 min. The solution containing the TML was applied 17"height×2"dia Dowex50W×8 column (H+ form). The column was washed with 500 ml of distilled water. This process was repeated with 1700 ml water and 1000 ml and 700 ml fractions were collected. Subsequently, 2M ammonium hydroxide solution was run and 8 fractions (each fraction 400 ml) were collected. TLC was checked of all the fractions (tic system:MeOH:water:Acetic acid::80:10:10). Eight fractions were combined and evaporated to get oil. The oil was subsequently lyophilized to get solid. The solid was triturated in acetonitrile and the solid was filtered and washed with acetonitrile again. The solid was dissolved in methanol/water (95:5:: Methanol:dd Water) and filtered with glass micro filter paper and filtrate evaporated and lyophilized.

A bigger scale synthesis has been achieved, which is further amenable to larger scale production of TML. The bigger scale synthesis of TML incorporating step of final clean up to achieve purity of at least 98% or greater, and free of foreign materials, has been demonstrated. The literature procedure does not teach synthesis of high purity TML, which could be applicable to pharmaceutical grade product.

Thus, the purification steps that allow larger scale synthesis can be described as follows:
1. Run crude TML through an ion exchange resin column;
2. Wash the ion exchange resin column with at least 4 times the volume of water as the amount of present crude TML;
3. Elute the washed TML from the ion exchange resin column. Freeze the eluted solution and then lyophilize at room temperature to prevent or minimize any decomposition of obtained TML; and
4. Triturate the lyophilized solid TML.

In another embodiment, the following steps are included:
5. dissolve the triturated TML into a polar solvent;
6. filter the dissolved TML through a microglass membrane filter; and
7. lyophilize the filtered TML at room temperature.

This Process Is An Improvement Of What Is Disclosed In Frederic M. Vaz, Bela Melegh, Judit Bene, Dean Cuebas, Douglas A. Gage, Albert Bootsma, Peter Vreken, Albert H. Van Gennip, Loran L. Bieber And Ronald J. A. Wanders, Clin. Chem. 48:6, 826-834, 2002.

Quality Control: the Following Quality Control Parameters were Obtained.

TLC: Samples 1 and 2 were purified TML made according to the invention. Sample 3 was a reference TML purchased from Sigma-Aldrich. The tic plates were Baker-flex silica gel IB-F. TLC Purity: was greater than 99%, and the spots were observed after staining the spot with ninhydrin (10% in methnol) (FIG. 1).

Figure 2A:
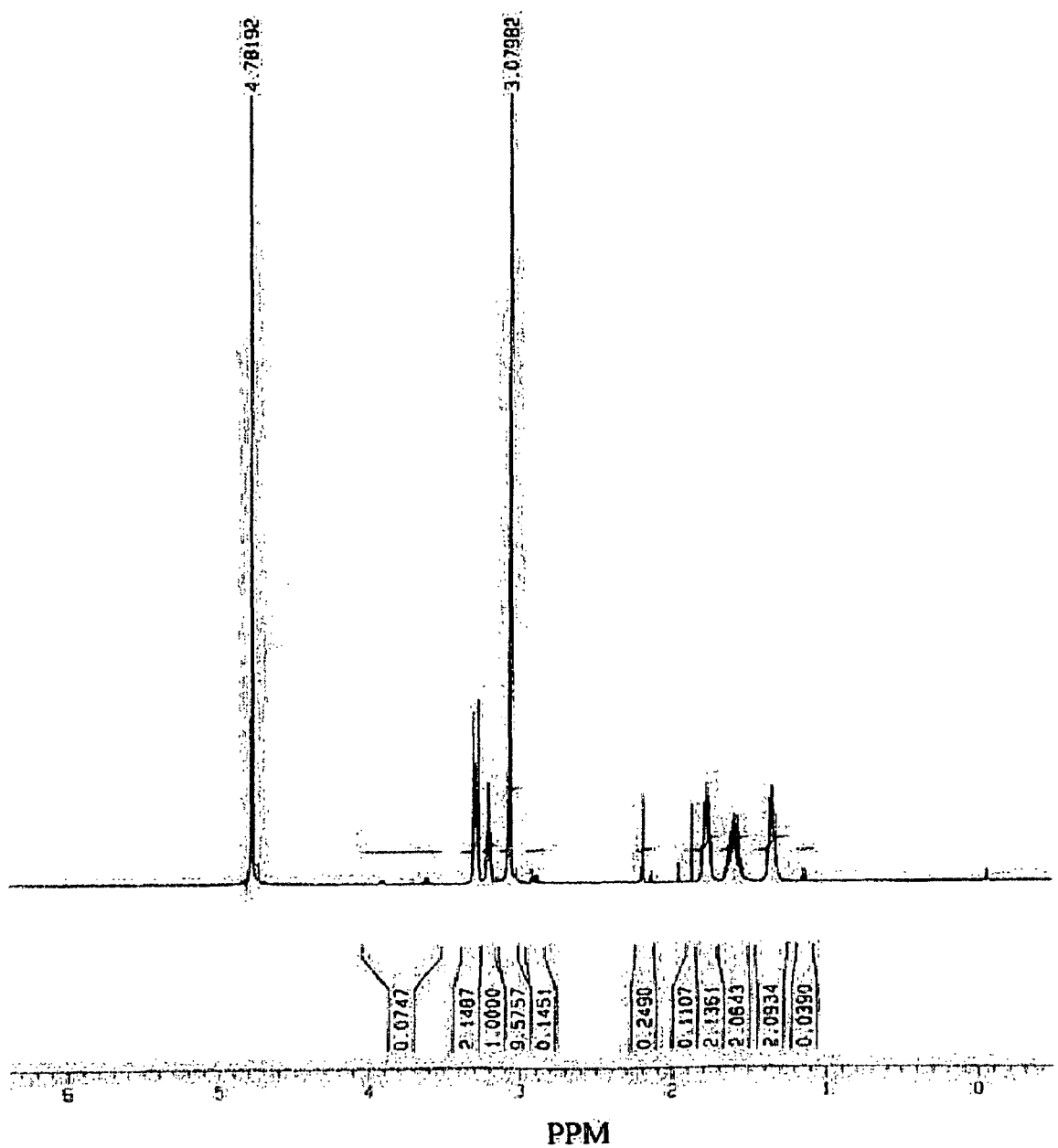
FIGS. 2a and 2b show $^1$H NMR data for synthesized and purified TML.
Figure 2B:
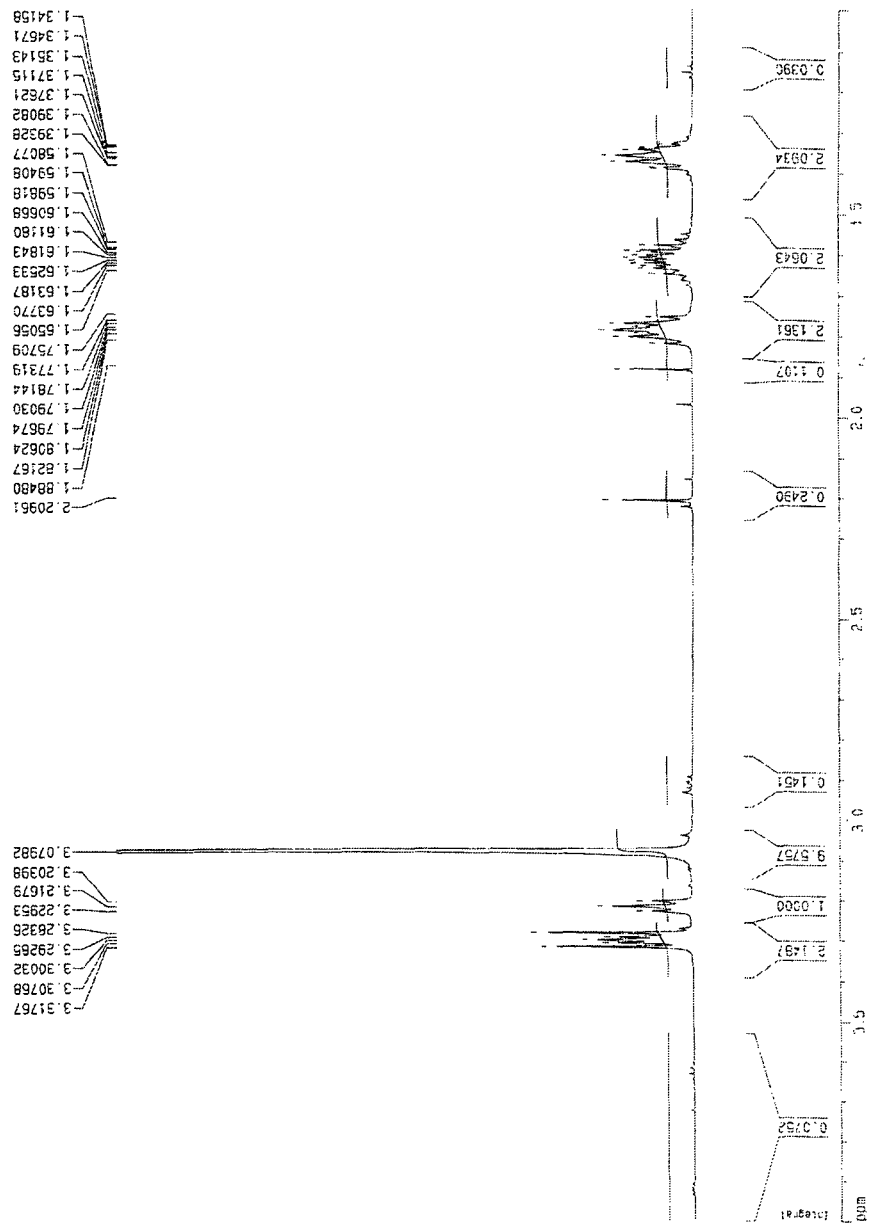

$^1$H NMR: The $^1$H NMR (Proton in $D_2O$) was run on 300 MHz; 1.3932 ppm (methylene at C-2; 2H; broad singlet), 1.6643 ppm (methylene at C-3; 2H, broad, multiplet); 2.13 ppm (methylene at C-4; 2H, broad singlet), 3.2928 ppm (methylene proton at C-5, 2H; triplet); 3.2167 ppm (alpha H; 1H; triplet); 3.0798 ppm (trimethyl H's; 9H) (FIGS. 2a and 2b).

Figure 3:
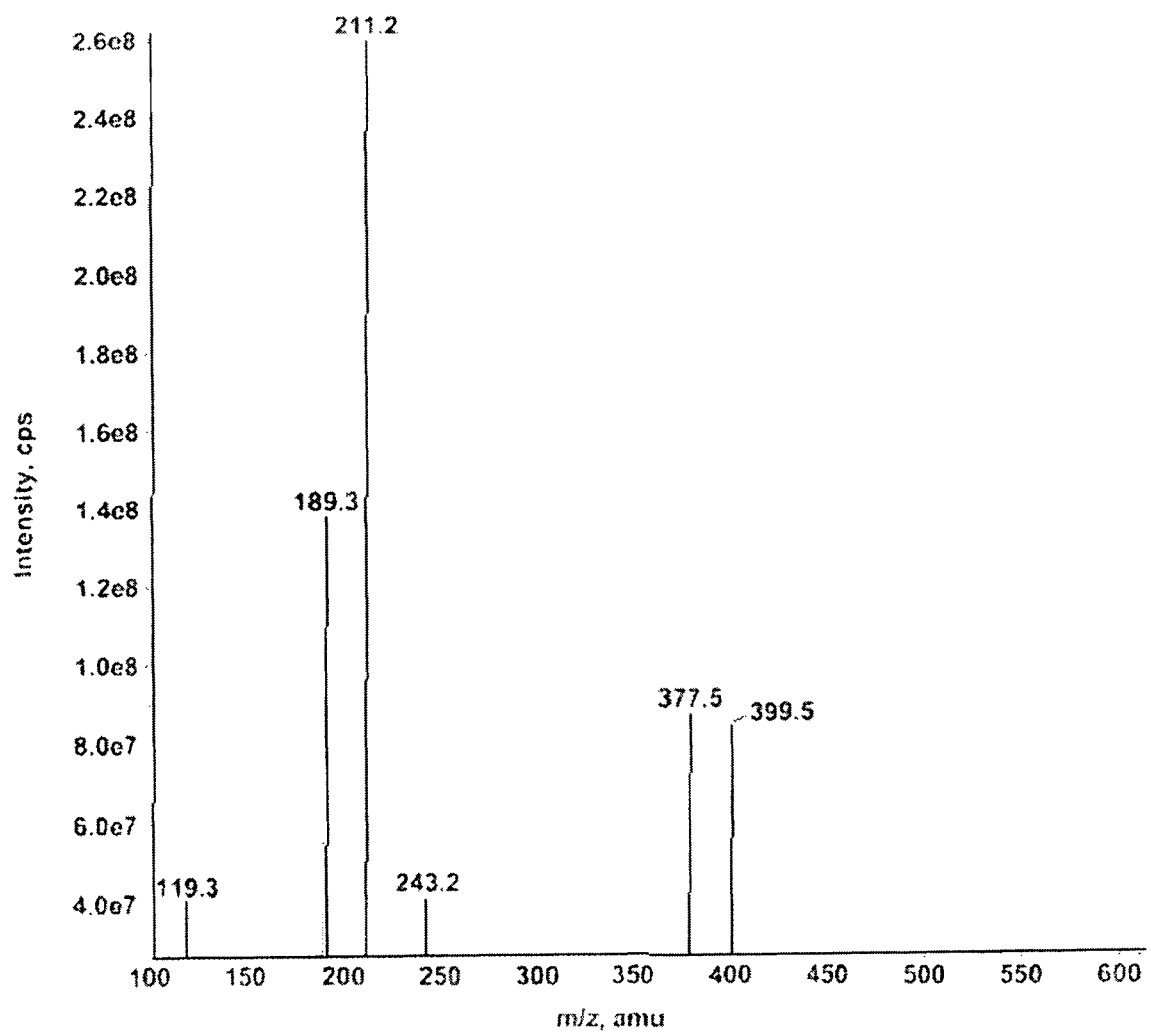
FIG. 3 shows Mass Spectrum data (positive ion) for synthesized and purified TML.

Mass Spectrum: Chemical formula $C_9H_{20}N_2O_2$, Molecular weight; 189.28. Four major fragmentation peaks were observed in positive mode; m/e 189.3, m/e 211.2 (+Na ion), m/e 377.5 (possibly dimer formation) and m/e 399.5 (possibly Na+ ion addition on dimmer) (FIG. 3).

Salt Formation

The TML synthesized (as described above) had no external salt. The carboxylic group (which is negatively charged) and the trimethyl group (which is positively charged) form an internal salt. The alpha amino group picks up the proton from the ionized carboxylic group. The molecular weight of this TML is 188.3 From our Mass Spectral analysis (positive ion) we get the molecular ion peak at 189.28 (One extra mass in positive ion is proton adding from matrix). This data confirms MW of 188.3.

The skilled artisan will understand that TML can exist as an external salt as well, such as a potassium salt.

2. Prophetic Example of Synthesis of TML-Carboxylic Acid Esters (Formula II, Below)

As shown in equation 1, the conversion of carboxylic group of the TML carboxylic group will be achieved by acid catalyzed nucleophilic addition of methanol, ethanol and higher alcohol homologs to produce methyl ester (R'; CH3), ethylester (R'; C2H5), and higher ester respectively.

The TML methyl ester (III; R';CH3) can be prepared by taking a suspension of TML in excess methanol, followed by saturation of the reaction mixture with anhydrous hydrogen chloride. The mixture is to be evaporated and the excess of HCL to be removed, to give crude solid. The mixture can then be neutralized carefully to neutral pH. In the absence of free carboxylic acid, the quarternary ammonium nitrogen of TML methyl ester would form a hydroxide salt. The crude product can subsequently be purified by ion exchange chromatography to get pure TML methyl ester.

The higher ester homologs (III; R'; C2H5, C3H7 n and iso, C4H9, n and iso, pentyl, n and iso) can be similarly prepared under similar reaction condition. The aromatic esters can be similarly prepared. The esterification reaction generally takes longer reaction time in presence of anhydrous HCl (equation 1).

The reaction can be shown as follows, with R' as defined above.

Equation 1. Esterification of TML

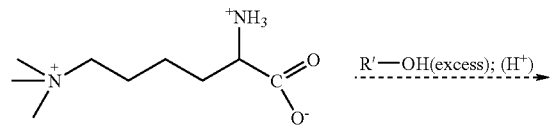

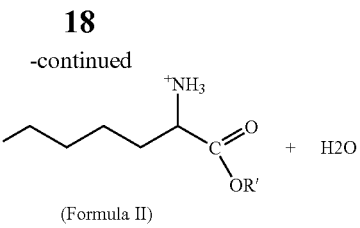

(Formula II)

3. Prophetic Example Synthesis of TML-Carboxylic Acid Esters and Amides (Formula IV)

As shown in Equation 2, below, the synthesis of amidites of TML-carboxylic acid esters can be achieved in a straightforward manner from the formula III, below, under mild basic conditions using dilute NaOH, dilute KOH, dilute barium hydroxide, or tertiary amines such as, triethylamine, diisopropyl ethylamine, and protection of the alpha-amino group with aliphatic and aromatic acid chlorides or acid anhydride, followed by neutralization of excess base, extraction of protected TML, and ion-exchange chromatography. The trimethylammonium group of the compounds formulas V, would exist in the salt form. The acid chloride could be chosen from a group of R" protecting groups, represented by R", such as acetyl chloride, ethyl acetyl chloride, propyl acetyl (normal and iso) chloride; butyl acetyl (normal and branched) chloride; pentyl acetyl (normal and branched) chloride or the corresponding acid anhydrides. Further the acid chloride could be from a group, such as compounds represented by trifluoromethyl acid anhydride, trichloromethylacetic anhydride, and further various aromatic, substituted aromatic, heterocyclic, substituted heterocyclic acid chloride can be taken for the substitution and protection of the alpha amino group of TML derivative represented by formula III. The higher homologs of formula V can similarly be prepared.

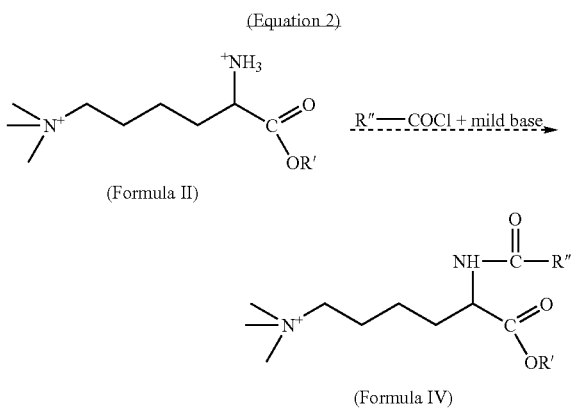

4. Prophetic Example of Synthesis of TML-Amides (Formula III)

As shown in equation 3, below, the synthesis of amidites of TML-carboxylic acid (formula IV) can be similarly be achieved best from TML under basic conditions using dilute NaOH, dilute KOH, dilute barium hydroxide, or tertiary amines such as, triethylamine, diisopropyl ethylamine, and aliphatic and aromatic acid chlorides or acid anhydride, followed by treatment of the reaction mixture with water to hydrolyze the mixed anhydride formed on the carboxylic function. This step was followed by extraction of protected TML, and ion-exchange chromatography. The trimethylammonium group of the compound of formula IV, would preferably exist in the internal salt form. R" is an alkyl having 1 to 5 carbon atoms or $CF_3$. In another embodiment, the acid chloride is trifluoromethyl acid anhydride and trichloromethylacetic anhydride. The skilled artisan will understand that the same or similar reaction can be carried out with R" being an aromatic ring, a substituted aromatic ring, a heterocyclic ring, and a substituted heterocyclic ring, the acid chloride of these can thus protect the alpha amino group of TML derivative represented by formula III. The higher homologs of formula V can similarly be prepared.

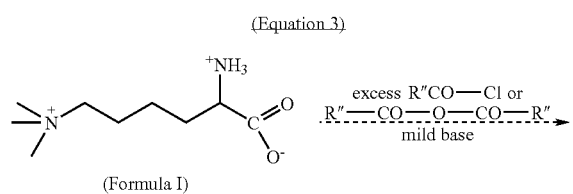

(Formula I)

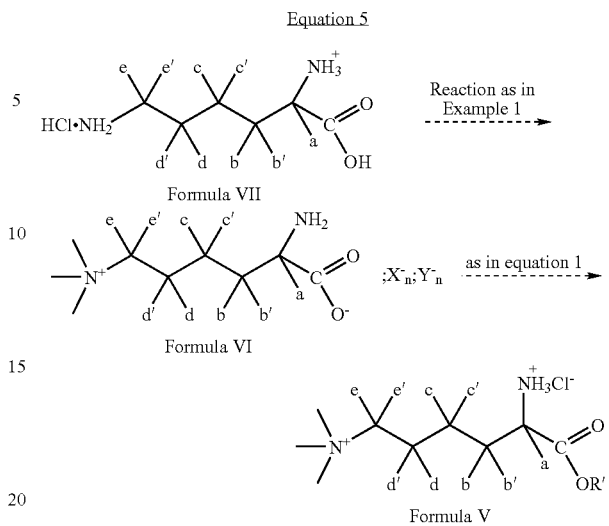

(Formula III)

5. Prophetic Example of Synthesis of Aliphatic Chain Substituted TML (Formula VI)

As depicted in equation 4, below, the synthesis of aliphatic chain substituted TML can best be obtained starting with aliphatic chain substituted L-lysine. Many such derivatives of Lysine are available. Thus as an example, tetradeutrated L-lysine (L-lysine 4,4,5,5-D4 L-lysine 0.2HCl)

Compounds within formula (VII) are commercially available from Cambridge Isotope Laboratories Inc., Andover, Mass. Additional deutrated L-Lysine can similarly be obtained commercially or custom produced by such companies. From such aliphatic chain modified L-Lysine, aliphatic chain modified TML can be produced by the method outlined in the method of synthesis of TML in the present invention. Since the aliphatic chain substitutions proposed in claim are chemically non reactive, the L-Lysine to TML conversion would follow straightforward similar to our example of TML synthesis. The value of a, b, b', c, c', d, d', e, e' can independently be selected from the group consisting of H, deuterium, methyl, ethyl, propyl (normal and iso), butyl (normal and branched), and pentyl (normal and branched). Subsequently the carboxylic group could be esterified as exemplified in equation 1, above, leading to synthesis of compounds with R' being H, deuterium in one or more carbons of the aliphatic chain of TML, methyl; ethyl; propyl (normal and iso); butyl (normal and branched); pentyl (normal and branched). Further, R' could be aromatic, substituted aromatic, heterocyclic, substituted heterocyclic, can be synthesized similarly.

Synthesis of l-lysine, having carbon bound deuterium and $N^{15}$ labelled L-lysine can be achieved using the procedure as demonstrated by Weissman and Schoenheimer (N. Weissman, R. Schoenheimer, J. Biol. Chem. 140, 549, 1943). The procedure, which consists of a multistep process, allows deuterium and $N^{15}$ labeling in the process. With appropriately labeled lysine, the synthesis of appropriately labeled TML will proceed as demonstrated in Equation 1, outline in the improved process of making TML.

The selective synthesis of esters of TML, and other derivatives, as shown in the above examples can be achieved based on the principle and practical details abundant in literature for selective esterification of the carboxylic acid functionality of large number of amino acids. The details can be found in a number of text books of amino acid chemistry, such as (i) Amino Acid Derivatives, A Practical Approach, Editor Graham C. Barrett, Oxford University Press, 1999 (ii) Amino Acids and Peptide Synthesis by John Jones, Oxford University Press, 1992.

7. Delivery of TML to a Child Diagnosed with Late Infantile Neuronal Ceroid Lipofuscinosis (LINCL) (Patient; Female, Age 6. Weight; 27 lbs, Length: 36 Inches)

Child had been taking the supplements/vitamins listed in Appendix B for about three years before the start of TML therapy. In addition, she had been taking clonazepam (5-(2-chlorophenyl)-1,3-dihydro7-nitro-2H-1,4-benzodiazepin-2-one) which is sold under the trade name Klonopin by F. Hoffmann-La Roche Ltd. (Basel, Switzerland) for control of constant Myoclonic seizures for about the same time according to the following daily dosage: (a) at waking: ½ of one 0.5 mg tablet, (b) Every four hours after waking, ¼ of one 0.5 mg tablet, (c) At bedtime: ½ of one 0.5 mg tablet. She also took one (1) 25 mg capsule of nitrofurantoin macrocrystals (sold under the name Macrodantin by Procter & Gamble Pharmaceuticals, Cincinnati Ohio) once per day.

"Baseline" blood work was done after an overnight fast on the morning of Nov. 19, 2003. Child received her usual supplements/vitamins, clonazepam, and macrodantin. TML, as synthesized in Example 1 was given to the patient (5 mg of TML per day for a 30 day period, ending Dec. 28, 2003). Between Dec. 28, 2003 and Jan. 24, 2004 we gave an alternating daily dose of 5 mg/day and 10 mg/day. On Jan. 24, 2004 and till the "new" blood work was done on Jan. 29, 2004, the patient received 10 mg/day by usually taking 5 mg of TML with breakfast and 5 mg of TML with dinner. She received 5 mg per dose during the duration of the experiment. In other words, she received TML once per day on days that she received 5 mg, and TML twice per day on days that she received 10 mg of TML. The TML was administered in powder form intermixed with her food.

Child's General Physical Condition Before the Start of TML Therapy (Based on Parents' Observations):

1. Unable to talk since age 2
2. Unable to walk since age 2½.
3. Seizures (Myoclonic) began at approximately the age of 2 and ¾.
4. Genetically Diagnosed with Williams Syndrome at age 2½.
5. Was genetically diagnosed with Late Infantile Neuronal Ceroid Lipofuscinosis at age 4¼.
6. Had been fed food of a pureed consistency via an oral syringe. There is no feeding tube.
7. She had been taken care of at home by her biological mother and father.
8. The patient was legally blind. LINCL disease marker of "Bull's Eye Maculopathy" is present. Albeit slow, she still showed a pupillary response to light. Right eye sometimes did not respond as well as the left eye.
9. Was physically "Dystonic". Unable to hold herself up in a standing or sitting position. No meaningful control of arms, legs, feet or torso. Small amount of head control when held upright by mother or father in an upright position. Very "Hypertonic" in hands/fingers, arms, legs and ankles/feet.
10. Had recurrent Urinary Tract Infections
11. Was chronically constipated. Mother or father gave her an enema approximately every two days to avoid an impacted bowel, or worse.
12. Lived with constant insomnia. The child's sleep (and the parents' sleep) was interrupted between 1 and 3 times per night, almost every night for almost the past four years. This had gotten to the worst level we had seen before the TML therapy and according to what we knew, was destined to get worse (outside of a viable therapy).
13. The patient was chronically "Cyanotic" visibly in her hands and feet where they would regularly turn various shades of purple, red and blue for extended periods of time.
14. Her ability to swallow worsened as the disease wore on, and the parents ordered a suction machine to help her clear her saliva. At the time just before the beginning of TML therapy, mother and father used the machine 6 to 12 (approx) times a day to clear mucous and food. The patient has never aspirated food or anything else to our knowledge.
15. Before TML therapy, the child exhibited "Ptosis" of her eyelids (lids halfway down the eye) for much of the day and her general "alertness" was low.

Result after the TML Therapy:
(The Physical Appearance of the Patient After the Stated 9 Weeks of TML Therapy.)

1. After approximately the first two weeks of TML, the patient slept through the night every night with one exception. (One night she did wake up at 4 am—she was hungry), The insomnia was gone!
2) The child is now moving her bowels on her own one to three times a day (approximately) as opposed to going two or three days without bowel movement and us having to give her an enema. We are giving her an enema about once a week to make sure she is comfortable. With increased doses of TML and corresponding increases in bodily activities, enema was resumed 2 to 3 times per week.
3) We are observing virtually no cyanosis (or "cyanosis like") symptoms in the hands and feet. Even in frigid weather, her hands and feet are the same color as her arms and legs.
4) We are seeing more eye movement and even the emergence of "purposeful" eye movement and a faster pupillary response. If she is looking left, and somebody stands on her right and asks her to look at the person, it may take her a minute, but she is beginning to regularly do it!
5) Swallowing is very much improved, almost normal. She is now able to pretty much clear her throat by using a purposeful, strong cough. We are still using the suction machine during the day. With increased body activity (hyper-salivation due to teeth eruption), we have resumed 6-12 times per day use of the suction machine for safety reasons.
6) Legs are still "hypertonic". However, we are seeing a notable reduction in the hypertonicity of the child's arms, and hands and fingers. (This was also observed by a physiatrist and neurologist.)
7) In the office visit to the physician (neurologist) Jan. 30, 2004 she told us that the patient looked healthy. Very importantly, the physician noted that the patient's myoclonic seizures were markedly reduced in severity and in number and that when the physician touched the patient, it no longer elicited a full body jerk (Myoclonus). She noted how calm the patient was. This is indeed VERY important as the guaranteed long-term clinical endgame for a child affected with LINCL is intractable, unstoppable seizures (no matter what kind of seizure medication or how high a dosage one gives) and death.

The child's bloodwork results are in table 1, below and the empirical nature of the child's improvement is evidenced by the follow up blood results. These blood tests were standard clinical tests carried out at Children's Hospital of Pittsburgh.

TABLE 1

| Test Name | Nov. 19, 2003 | Clinical Range | Jan. 29, 2004 | Clinical Range |
|---|---|---|---|---|
| Hgb | 14.4 | high | 14 | normal |
| HCT | 42 | high | 40.3 | normal |
| RDW | 11.5 | high | 12.3 | normal |
| ABS Lymphocytes | 2.2 | low | 2.5 | normal |
| Glycine | 50 | high | 25 | normal |
| Taurine | 24 | high | 19 | normal |
| Carnitine, Total | 40 | normal | 43 | normal |
| Carnitine, Esthers | 7 | normal | 10 | normal |
| Alanine | 87 | high | 47 | normal |
| Carbon Dioxide | 32 | high | 22 | normal |
| BUN | 2 | low | 5 | (low) (6 is norm!) |
| AST | 60 | high | 50(high) | (40 is norm) |
| Platelets | 586 | high | 461 (high) | (369 norm) |
| Glutamine | 99 | high | 70 | normal |

Notes to the Table 1:
(a) HGB = hemoglobin, HCT = Hematocrit, RDW = Red Cell Distribution Width, ABS = absolute, BUN = Blood Urea Nitrogen, AST = Aspartate Amonotransferase)
(b) The examining physicians comments of Nov. 19, 2003 regarding table 1: (i) Alanine is elevated, this may be seen in states with increased pyruvate, (ii) Glutamine is increased, this may be seen, with Hyperammonemia.; Clinical correlation is indicated.
(c) The examining physicians comments on Jan. 29, 2004 that no significant elevation of serum amino acid was seen.
(d) The patient's glucose and potassium increased (Glucose 93 baseline to 132; Potassium 4.4 baseline to 4.8). Even though the follow up blood work was done after an all night fast, we did give her some "Gatorade" to drink before the blood test. This was given with her Klonopin to wash it down and certainly could be a contributing factor to the rise in glucose and potassium.

After Jan. 29, 2004, her parents continued giving her TML in varying doses (5 mg-30 mg) per day. The varying doses were based on the family's attempt to find an optimal dose. Her condition has remained stable through January 2005.

Discussions of TML Biosynthesis:
Occurrence of N-6-Trimethyl-L-lysine (TML), Biosynthesis & Metabolism:

The enzyme Tripeptidyl Peptidase1 (TPP1) is responsible for cleaving "Protein bound N-6-Trimethyl-L-lysine" with the resulting products of free TML and amino acids in normal people. However in children who have Late-Infantile neuronal ceroid lipofuscinoses (LINCL), the TPP1 is defective and the "Proteins bounded TML" is not broken down (M. L. Kaz, Biochem. Biophy. Acta, 1317, 192-198, 1996). It therefore becomes the storage material in the lysosome. Eventually it builds up in, and then "blows up" the lysosome causing eventual massive neuronal damage in brain and eventually death (P. Gupta and S. L. Hofmann, Molecular Psychiatry, 7, 434-436, 2002).

It has been shown that there is specific accumulation of a hydrophobic protein, subunit c of ATP synthase, in lysosomes from the cells of patients with the late infantile form of NCL (LINCL), and is caused by a defect in the CLN2 gene product, tripeptidyl peptidase I (TPP-I). The data by the authors show that TPP-I is involved in the initial degradation of subunit c in lysosomes and suggest that its absence leads directly to the lysosomal accumulation of subunit c (Ezaki, J., Takeda-Ezaki, M., Kominami, E., J Biochem (tokyo) September, 128(3), 509, 2000).

Lysosomal hydrolysis of these proteins results in the release of TML, which is the first metabolite of L-carnitine biosynthesis. Hepatic synthesis of carnitine takes place from protein-bound N-6-trimethyl-L-lysine. Lysosmal digestion of methyl-lysine labelled asialo-fetuin was carried out (LaBadie, J., Dunn, W. A. and Aronson Jr, N. N. Biochem. J. 160, 85-95, 1976). L-Carnitine biosynthesis has been studied, such as, from gamma-butyrobetaine and from exogenous proteine-bound-6-N-trimethyl-L-lysine by perfused guinea pig liver. In this connection the effect of ascorbate deficiency on the in situ activity of gamma-butyrobetaine hydroxylase was demonstrated (Dunn, W. A., Rettura, G., Seifter, E. and Englard, S., J. Biol. Chem. 259, 10764-10770, 1984).

Various Steps and the Enzymes Involved in the Pathway Leading from TML to L-Carnitine are Outlined in the Subsequent Paragraphs.

TML is first hydroxylated on its 3-position to form 3-hydroxy-N-6-trimethyl-L-lysine (HTML). The aldolytic cleavage of HTML with HTML Aldolase (HTMLA) yields trimethylaminobutyraldehyde (TMABA) and glycine. Dehydrogenation of TMABA by TMABA dehydrogenase (TMABA-DH) results in the formation of 4-N-trimethylaminobutyrate (butyrobetaine). In the last step, gamma-butyrobetaine is hydroxylated on the 3 position by gamma-butyrobetain deoxygenase (BBD; EC) to yield L-carnitine (Frederic M. Vaz and Ronald J. A. Wanders, Biochem. J. 361, 417-429, 2000). Very little is known about HTMLA. It might be identical to serine and glycine hydroxymethyltransferase (SHMT) which catalyses the tetrahydrofolate-dependent interconversion of serine and glycine (Girgis, S., Nasrallah, I. M., Suh, J. R., Oppenheim, E., Zanetti, K. A., Mastri, M. G. and Stover, P. J., Gene 210, 315-324, 1998). Purification and characterization of cytosolic and mitochondrial serine hydroxymethyltrasferase from rat liver was carried out (Ogawa, H. and Fujioka, M. J. Biochem. (Tokyo) 90, 381-390, 1981). SHMT also catalyses the aldol cleavage of other beta-hydroxylamino acids in absence of tetrahydrofolate, including HTML (Girgis, S., Nasrallah, I. M., Suh, J. R., Oppenheim, E., Zanetti, K. A., Mastri, M. G. and Stover, P. J. Gene 210, 315-324, 1998). Synthesis of butyrobetaine and L-carnitine from protein bound TML is inhibited by 1-amino-D-proline, an antagonist of vitamin B6. This inhibitory effect of 1-amino-D-proline on the production of L-carnitine from exogenous protein-bound N-6-trimethyl-L-lysine by the perfused rat liver was shown by (Dunn, W. A., Aronson Jr, N. N. and Englard, S., J. Biol. Chem. 257, 7948-7951, 1982).

It is well known from the biochemistry of the metabolic pathway of TML to HTML, that certain cofactors; such as 2-oxoglutarate, Fe2+, molecular oxygen and ascorbate have to be present. Similarly in the subsequent steps of metabolic pathway from HTML to L-Carnitine, the biochemically defined cofactors have to be present. The cofactors (2-oxoglutarate, Fe2+, molecular oxygen, and ascorbate) have been established by a number of researchers during the enzymatic hydroxylation of TML. It is likely that other chemicals will work as cofactors as well. For example, DTT (dithiothreitol) has been used instead of ascorbic acid (which is required to keep Fe2+ in reduced form), in test tube conditions. Besides the aforesaid cofactors, calcium ion was found to cause significant enhancement in the conversion of TML to HTML (D. S. Sachan, C. L. Hoppel, Biochem. J., 188, 529-534, 1980).

4-N-trimethylaminobutyraldehyde dehydrogenase (TMABA-DH) catalyses the dehydrogenation of 4-N-trimethylamino butyraldehyde to butyrobetaine. TMABA-DH has an absolute requirement for NAD+. In human tissues, the rate of TMABA dehydrogenation is highest in liver, substantial in kidney, but low in brain, heart and muscle (Rebouche, C. J. and Engel, A. G., Biochim. Biophys. Acta, 22-29, 1980). The purification of TMABA-DH was carried out from beef liver (Hulse, J. D. and Henderson, L. M., Fed. Proc. Fed. Am. Soc. Exp. Biol., 38, 676, 1979).

Gamma-Butyrobetaine dioxygenase (BBD) catalyses the stereospecific hydroxylation of butyrobetaine to L-Carnitine in mammalian studies. BBD activity was stimulated considerably by 2-oxoglutarate, and the enzyme requires molecular oxygen, $Fe^{2+}$ and ascorbate for activity. (Lindblad, B., Lindstedt, G. and Tofft, M., J. Am. Chem. Soc., 91, 4604-4606, 1969). BBD activity has been found to be localized in the cytosol.

Kakimoto and Akazawa were the first to identify TML in human urine. All methods to assay TML in either plasma, urine or tissue samples use the same sample work-up. The concentration of TML in plasma is relatively constant in both human and rat, ranging from 0.2 to 1.3 micromole. Plasma levels of TML have been shown to correlate with body mass. In humans, urinary TML concentration is proportional to that of creatine. Furthermore TML is not reabsorbed by kidney in humans (Davis, A. T., Ingalls, S. T. and Hoppel, C. L J. Chromatogr. 306, 79-87, 1984.). In humans, TML concentrations range between 2 to 8 micromole/per mmole of creatinine. (Kakimoto, Y. and Akazawa, S., J. Biol. Chem. 245, 5751-5758, 1970).

Butyrobetaine is the last step in the synthesis of L-carnitine. The level of butyrobetaine in urine is low (~0.3 micromole/mmol creatinine) (F. M. Vaz, B. Melegh, J. Bene, D. Cuebas, D. A. Gage, A Bootsma, P. Vreken, A. H. van Gennip, L. L. Bieber and R. J. A. Wanders, unpublished work) compared with the concentration in plasma 4.8 micromole (Sandor, A., Minkler, P. E., Ingalls, S. T. and Hoppel, C. L., Clin. Chim. Acta., 176, 17-27, 1988).

Factors in the Biosynthesis & Control of L-Carnitine and N-6-Trimethyl-L-lysine:

Major sources of L-carnitine in the human diet are meat, fish and dairy products. Omnivorous humans generally ingest 2-12 micromole of L-carnitine per day per kg of body weight. This is more than the L-carnitine produced endogenously, which has been estimated to be 1.2 micromole per day per kg of body weight. In omnivorous humans, approx.75% of body L-carnitine sources come from the diet and 25% comes from de novo biosynthesis. Since L-carnitine is present primarily in foods of animal origin, strict vegetarians obtain <0.1 micromol per day per kg of body weight. Strict vegetarians obtain more than 90% of their L-carnitine through biosynthesis.

Two primary intermediates have been proposed as the factors which limit biosynthesis of L-carnitine via their availability. These two intermediaries are g-butyrobetaine and N-6-trimethyl-L-lysine. Studies have shown that increasing the amount of either of these two intermediates in the bloodstream will increase the production of L-carnitine 100-fold in rats and 3-fold in human infants & adults (Olson and Rebouche, J. Nutr. 117(6), 1024-31, 1987). Thus L-carnitine biosynthesis may be regulated by one or all of the three enzymes which, together, catalyze the transformation of N-6-trimethyl-L-lysine into g-butyrobetaine. The high level of L-carnitine synthesis from exogenous L-carnitine precursors suggests that the enzymatic capacity to synthesize L-carnitine from TML and butyrobetain is much higher than is usually utilized. This suggests that only the availability of TML is the rate limiting step in the regulation of feedback inhibition for L-carnitine biosynthesis (Scheme 1). (F. M. Vaz and R. J. A. Wandars, Biochem. J., 361, 417-429, 2002).

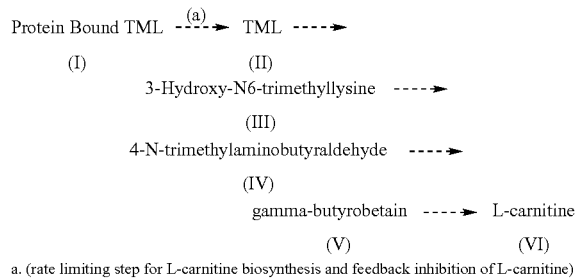

Scheme 1.
Biosynthesis of L-Carnitine from TML
(feedback regulation of TML)

a. (rate limiting step for L-carnitine biosynthesis and feedback inhibition of L-carnitine)

L-ascorbic acid may be a principle co-factor in the metabolism of L-carnitine. It has been postulated and demonstrated that an experimental vitamin C deficiency resulted in increased urinary excretion of L-carnitine. This increased excretion of L-carnitine may be due to either decreased absorption from dietary sources, or increased excretion from the kidney. Several methods have been described to measure the concentration of L-carnitine biosynthesis metabolites in biological fluids and tissues.

The kidney plays a major role in L-carnitine biosynthesis, excretion and acylation. Unlike in the rat, human kidney contains all enzymes needed to form L-carnitine from N-6 trimethyl-L-lysine in activities exceeding those of the liver (K, Doqi, National Kidney Foundation. Am. J. Kidney Dis., 35, 6 Suppl 2 S1-140, 2000). This L-carnitine precursor, TML, is found to be increased in plasma of patients with chronic renal failure. Free L-carnitine formed in the kidney as well as L-carnitine reabsorbed from the glomerular filtrate may be acylated in the proximal tubule. Isolated rat cortical tubule suspensions contain total L-carnitine concentrations of 2.85 micromols/g protein. During incubation over 60 min the acylcarnitine/carnitine ratio decreased, indicating deacylation of acylcarnitine in proximal tubules. Exogenous L-carnitine was acylated at a rate of 35 micromols/h/g protein. Besides pyruvate and acetate, ketone bodies stimulated the acylation rate several fold, indicating that these substrates are a major source of acetyl-CoA for the acylation reaction. This may explain the higher acetylcarnitine/L-carnitine ratio found in urine under ketotic conditions.

However later data show that although all the enzymes may reside in kidney, all the metabolites and enzyme reside in brain only, where active synthesis of L-carnitine from TML takes place (F. M. Vaz and R. J. A. Wandars, Biochem. J., 361, 417-429, 2002). The concentration of butyrobetaine in plasma and tissues was determined by isolating butyrobetaine via HPLC or ion-exchange chromatography, and using BBD to convert it into L-carnitine In humans, the level of butyrobetaine in urine is low (~0.3 micromole/mmole L-creatinine) compared with the concentrations in plasma (4.8 mmole & 1.8 mmole).

The concentration of L-carnitine in plasma from both humans and rats is age and sex dependent. In humans, the plasma L-carnitine concentration increases during first year of life (from ~15 to ~40 mmole), and remains the same for both sexes until puberty. From puberty to adulthood, plasma L-carnitine concentrations in males increases and stabilizes at a level that is significantly higher than those in females (50 compared with 40 micromole).

Roles of L-Carnitine:

A summary of the role of carnitine is outlined as follows:

(a). From a biochemical standpoint, L-carnitine plays an essential role in energy metabolism. In fatty acid metabolism, it serves as shuttle between the cell sap and the mitochondria inner-workings permitting breakdown of the long carbon fragment.

(b). The more important role is in maintaining a balance between the concentration of a compound called acyl CoA in the cell compartments. For sugar to be metabolized, they are sequentially degraded to smaller fragments until carbon dioxide is produced, along the way energy is conserved. Acyl CoA is an important intermediate in transfer of energy. Accordingly, it is important that the concentration of Acyl CoA be regulated and this function falls on L-carnitine. The role of L-carnitine and L-carnitine supplementation during exercise in man and in individuals with special needs has been illustrated (Brass E. P., Hiatt W. R., J. Am. Coll. Nutr., 17(3):207-215, 1998).

(c) Defects in fatty acid oxidation are a source of major morbidity and are potentially rapidly fatal. Fatty acid oxidation defects encompass a spectrum of clinical disorders, including recurrent hypoglycemic, hypoketotic encephalopathy or Reye-like syndrome in infancy with secondary seizures and potential developmental delay, progressive lipid storage myopathy, recurrent myoglobinuria, neuropathy, and progressive cardiomyopathy. (I. Tein, J Child Neurol. 2002 December; 17 Suppl 3:3S57-82; discussion 3S82-3).

(d) Supplementation or treatment of a number of these diseases/disorders with L-carnitine has had beneficial effects. For example, some researchers feel that L-carnitine supplementation may complement other therapies for the treatment of AIDS (Effect of L-carnitine on human immunodeficiency virus-1 infection-associated apoptosis; Moretti S., Alesse E., Di Marzio L., a pilot study. Blood, 91(10):3817-3824, 1998). According to the authors, the treatment of immunodeficiency virus type 1 infection/acquired immune deficiency syndrome (AIDS), may elicit or cause carnitine deficiency problems. Additionally, some epileptic patients may benefit from carnitine supplementation/treatment.

(e). L-Carnitine may be essential or "conditionally essential" for several groups of people including: normal infants, premature infants, and both children and adults suffering from a variety of genetic, infectious, and injury-related illnesses. For example, some cardiomyopathies which afflict children are due to metabolic errors or deficiencies. There is data that supports treatment of some myocardial dysfunctions with L-carnitine supplementation. (Winter, S., Jue, K., Prochazka J., Francis, P., Hamilton, W., Linn, L., Helton, E. (1995) J. Child Neurol. 10, Supple 2: S45-51.)

(f) Administration of L-carnitine prevents acute ammonia toxicity and enhances the efficacy of ammonia elimination as urea and glutamine. In addition the cytotoxic effects of ammonia, possibly arising from lipid peroxidation, are ameliorated by L-carnitine. These data indicate the feasibility of utilization of L-carnitine in the therapy of human hyperammonemic syndromes, both for reducing the levels of ammonia and preventing its toxic effects. (O'Connor J E, Adv Exp Med Biol. 1990; 272:183-95).

(g) L-Carnitine deficiency can be defined as a decrease of intracellular L-carnitine, leading to an accumulation of acyl-CoA esters and an inhibition of acyl-transport via the mitochondrial inner membrane. This may cause disease by the following processes:

(g1) Inhibition of the mitochondrial oxidation of long-chain fatty acids during fasting causes heart or liver failure. The latter may cause encephalopathy by hypoketonaemia, hypoglycaemia and hyper-ammonaemia. It was shown that acetyl-L-carnitine fed to old rats partially restores mitochondrial function and ambulatory activity (Hagen T M, Ingersoll R. T, Wehr C. M, Proc. Natl. Acad. Sci. USA., 95(16): 9562-9566, 1998).

(g2) Increased acyl-CoA esters inhibit many enzymes and carriers. Long-chain acyl-CoA affects mitochondrial oxidative phosphorylation at the adenine nucleotide carrier, and also inhibits other mitochondrial enzymes such as glutamate dehydrogenase, L-carnitine acetyltransferase and NAD transhydrogenase. (Scholte H R, J Clin Chem Clin Biochem. May 1990; 28(5):35.)

(g3) Accumulation of triacylglycerols in organs increases stress susceptibility by an exaggerated response to hormonal stimuli (Iyer, R. N., Khan, A. A., Gupta, A., Vajifdar, B. U., Lokhandwala, Y. Y., J Assoc Physicians India, 8(11):1050-1052, 2000).

(g4) Effects of L-carnitine on exercise tolerance in chronic stable angina: a multicenter, double-blind, randomized, placebo controlled crossover study (Cherchi, A., Lai, C., Angelino, F., et al., Int. J. Clin. Pharmacol. Ther. Toxicol., 23(10): 569-572, 1985).

(g5) Decreased mitochondrial acetyl-export lowers acetyl-choline synthesis in the nervous system.

(h) Primary L-carnitine deficiency can be defined as a genetic defect in the transport or biosynthesis of L-carnitine. Until now only defects at the level of L-carnitine transport have been discovered. The most severe form of primary L-carnitine deficiency is the consequence of a lesion of the L-carnitine transport protein in the brush border membrane of the renal tubules. This defect causes cardiomyopathy or hepatic encephalopathy usually in combination with skeletal myopathy. In a patient with cardiomyopathy and without myopathy, it was found that L-carnitine transport at the level of the small intestinal epithelial brush border was also inhibited. The patient was cured by L-carnitine supplementation. Muscle L-carnitine increased, but remained too low. This suggests that L-carnitine transport in muscle is also inhibited. L-Carnitine transport in fibroblasts was normal, which disagrees with literature reports for similar patients. W. R. Treem, C. A. Stanley, D. N. Finegold, D. E. Hale, P. M. Coates, N. Engl. J. Med, 319, 1331-1336, 1988; G. Karpati, S. Carpenter, A. G. Engel, G. Watters, J., Allen, S. Rothman, G. Klassen, O. A. Mamer, Neurology, 25, 16-24, 1975; B. O. Eriksson, S. Lindstedt, I. Nordin, Eur. J. Pediatr., 147, 662-663, 1988; H. R. Scholte, R. Rodrigues Periera, P. C. de Jonge, I. E. Luyt-Houwen, M. Verduin, J. D. Ross, J. Clin. Chem. Clin. Biochem. 28, 351-357, 1990; C. A. Stanley, S. DeLeeuw, P. M. Coates, C. Vianey-Liaud, P. Divry, J. P. Bonnefont, J. M. Saudubray, M. Haymond, F. K. Tretz, G. N. Breningstall, Ann. Neuro. 30, 709-716, 1991; Y. Wang, J. Ye, V. Ganapati, N. Longo, Proc. Natl. Acad. Sci. USA 96, 2356-23601999).

(i) Optimal ATP production from either dietary or stored fatty acids is dependent on L-carnitine. L-Carnitine has several roles, most of which involve conjugation of acyl residues to the b-hydroxyl group of the L-carnitine with subsequent translocation of this complex from one cellular compartment to another. In the CLN3, proteins have been found to cause modulation of the cell growth rates and apoptosis (Persaud-Sawin D. A., Van Dongen A., Boustany R. M., Human Molecular Genetics. II(18):2129-42, 2002). It has been shown that defects in soluble lysosomal enzymes causes Neuronal ceroid lipofuscinoses (CLN1 and CLN2). (Hofmann S. L., Atashband A., Cho S. K., Das A. K., Gupta P., Lu J. Y., Current Molecular Medicine. 2(5):423-37, 2002). It has been also shown that the conditions of Parkinson's disease are present when there is dysfunction in both striatal and nigral neurons and this dysfunction results in autosomal dominant adult neuronal ceroid lipofuscinosis (Nijssen, P. C., Brusse, E., Leyten, A. C., Martin, J. J., Teepen, J. L., Roos, R. A., Movement Disorders, 17(3):482-7, 2002). It has been shown that abnormal accumulation of specific proteins occurs in the neuronal ceroid lipofuscinosis/Batten disease. These conditions result due to defect in the lysosomal proteases and related enzymes. The phenomenon is commonly termed as lysosomal proteinoses. This abnormal accumulation of proteins in the lysosomes has been shown to be responsible for major diseases such as Alzheimer diseases, alpha-synuclein in Parkinson's disease, Lewy body dementia (Gupta, P., Hofmann, S. L., Molecular Psychiatry. 7(5):434-6, 2002). An autoantibody inhibitory to glutamic acid decarboxylase in the neurodegenerative disorder Batten disease has been reported (Chattopadhyay, S., Ito, M., Cooper, J. D., Brooks, A. I., Curran, T. M., Powers, J. M., Pearce, D. A., Human Molecular Genetics. 11(12): 1421-31, 2002). By mutations in different proteins result are similar in disease of neuronal ceroid lipofuscinoses. (Weimer, J. M., Kriscenski-Perry, E., Elshatory, Y., Pearce, D. A., NeuroMolecular Medicine. 1(2): 111-24, 2002). Lysosomal localization of the neuronal ceroid lipofuscinosis CLN5 protein. (Isosomppi, J., Vesa, J., Jalanko, A., Peltonen, L., Human Molecular Genetics. 11(8):885-91, 2002).

In summary, L-carnitine plays a key and critical role in enhancing fat metabolism. Reports attest to the fact that L-carnitine works by transporting fatty acids to be burned for fuel, increasing both energy supply and lean muscle mass. Most found that unless an individual is deficient in L-carnitine, it is an unnecessary ergogenic aid. This contrasts with the apparent need in Late Infantile Neuronal Ceroid Lipofuscinosis (LINCL-one form of Batten Disease) of the correct operation of the endogenous production of L-carnitine. This need was not ameliorated by the giving exogenous L-Carnitine to dogs with Batten Disease (Siakotos A. N., Hutchins G. D., Farlow M. R., Katz M. L., European Journal of Paediatric Neurology 5 Suppl A: 151-6, 2001). This also was not observed by the parents of the child who was afflicted with LINCL (discussed later). She was given exogenous L-carnitine for over three years without significant metabolic changes or marked outward observations of her condition. It was only the delivery of exogenous TML to the afflicted LINCL child that yielded significant metabolic and outward, observable changes to her condition.

Discussion of Results

1) Hyperammonemia—After the administration of TML, amelioration of the hyperammonemic condition witnessed by us (blue hands and feet) and in the clinical notes of the examining physician of Children's Hospital, who noted the clinical condition in his review of the blood work ("alanine is elevated, this may be seen in states with increased pyruvate, glutamine is increased, this may be seen with hyperammonemia. Clinical correlation is indicated"). Just as we saw her hands and feet return to normal coloration, the physician noted "No significant elevation of serum Amino Acids" in his review of the follow up blood work.

2) Decrease in Glutamine levels—The patient's baseline glutamine reading was 99 (high). After the administration of TML the follow up blood work showed a reading of 70 (normal!). This fact is important to note as we discuss the resolution of the condition of insomnia.

3) Insomnia—The first important external proof that the child's glutamine/Glutamate(Glutamic Acid) metabolism is normalizing is the amelioration of her previous condition of insomnia.

Typically, LINCL afflicted children get to a point in the disease continuum that they do not know day from night because of the degree of affect the disease has had on the brain stem. It is of more than just interest to note that those who are taking glutamine as a supplement for sports performance enhancement or to combat aging can experience "nervousness" and "insomnia" if the dose is too large. Glutamine by itself is not "excitatory". But Glutamine supplementation will cause the synthesis of glutamate, which is an excitatory neurotransmitter ("*Escherichia coli* and Salmonella, Cellular and Molecular Biology, 2nd Edition," American Society for Microbiology, Washington, D. C., 1996. The Glial cells (Astrocytes) are responsible for ridding the extracellular space of extra Glutamate. However, the conversion of Glutamate into Glutamine is a "one-way" pathway that is ATP dependent (Nucleic Acids Res. 30(1):59 2002-(see Schematic 2). In fact it looks like this:

(Schematic 2)

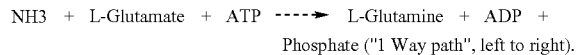

NH3 + L-Glutamate + ATP ----→ L-Glutamine + ADP + Phosphate ("1 Way path", left to right).

There are two very important items of note in this. First, if there is not enough ATP, then this transaction is unable to be completed. Second, if this transaction is not completed in the extracellular space, two items will remain in the extracellular space, Ammonia (NH3) and Glutamate. If too much NH3 accumulates then ultimately a state of "Hyperammonemia" will result (similarly to what we saw in the child). It is interesting to note that "The conversion of glutamic acid into glutamine is the only means by which ammonia in the brain can be detoxified" ("Prescription For Nutritional Healing, 3rd edition", Phyllis A. Balch, CNC and James F. Balch M.D. p. 47, Avery Publishing, New York, 2000). If too much Glutamate accumulates in the extracellular space, then there will be too much "excitatory" neurotransmitter. In sports supplementation mentioned above this may just be "nervousness". In a LINCL child who is already neurologically compromised, this may manifest itself as myoclonus?

What could we do to provide enough ATP in the above transaction (In an LINCL child)? Enter TML. Earlier, we noted that TML as the first of four metabolites in the carnitine Biosynthesis pathway. If it (TML) is not being synthesized in the body as previously hypothesized, then carnitine cannot be endogenously synthesized. If carnitine is not available (and for the sake of our discussion, endogenous carnitine since all four of the metabolites in the carnitine biosynthesis pathway reside in the brain), then appropriate oxidative phosphorylation (fatty acid oxidation) is not going to be efficient, if work at all. If oxidative phosphorylation is not operating properly, then its end product will be deficient, or virtually absent. This end product is ATP.

We have seen that if there is deficient/absent ATP, then glutamate will not be converted to glutamine and excess glutamate and ammonia will be the result. We believe that the results of amelioration of insomnia (clearing of glutamate), amelioration of hyperammonemia (clearing of ammonia) and the normalization of the glutamine level (a by product of high ammonia levels in the blood) and the overall glutamine/glutamate metabolism seems to be the direct result of TML therapy on the level of available ATP.

Obviously, carnitine is available from exogenous sources (meat, milk). However, work has been done to see if exogenous carnitine would ameliorate the symptoms of Juvenile (not LINCL) Neuronal Ceroid Lipofuscinosis. This research in dogs showed that it made the dogs more functional and they lived 10% longer than untreated dogs, but the dogs still died very young compared to unaffected dogs and brain glucose hypometabolism and cerebral atrophy were not reduced (Siakotis, Katz et al., European Journal Pediatric Neurology 5, (Suppl. A): 151-156, 2001). It is an exciting prospect to see that TML may indeed be that therapeutic agent to cause positive brain metabolism based upon the results we have seen.

While the present invention has been particularly described in terms of certain preferred embodiments, the invention is not limited to such preferred embodiments. Rather, the scope of the invention is defined by the appended claims.

The invention claimed is:

1. A method of treating a human being for a condition associated with a deficiency in the N-6-trimethyl-L-lysine (TML) pathway affecting biosynthesis of carnitine, by administration of a pharmaceutically acceptable salt of said N-6-trimethyl-L-lysine, wherein said condition is late infantile neuronal ceroid lipofuscinosis (LINCL) or neuronal ceroid lipofuscinosis (NCL).

2. The method of claim 1 of treating a human being, wherein said pharmaceutically acceptable salt of said N-6-trimethyl-L-lysine is N-6-trimethyl-L-lysine (TML) of at least 98% purity.

3. The method of claim 2 wherein said pharmaceutically acceptable salt of said N-6-trimethyl-L-lysine is a prodrug comprising an aliphatic chain derivative of N-6-trimethyl-L-lysine (TML), a carboxylic acid ester derivative of N-6-trimethyl-L-lysine (TML), or an alpha amino amide derivative of N-6-trimethyl-L-lysine (TML).

4. The method of claim 1, wherein said condition is associated with an impairment of carnitine or carnitine esters, or decreased fatty acid metabolism.

5. The method of claim 1, wherein said condition involves accumulation of neuronal autofluorescent storage bodies in lysosomes or neurons, or regression of motor development.

* * * * *